United States Patent [19]
Ramshaw et al.

[11] Patent Number: 5,866,131
[45] Date of Patent: Feb. 2, 1999

[54] RECOMBINANT VACCINE

[75] Inventors: Ian Allister Ramshaw, Duffy; David Bernard Boyle, Leopold; Barbara Elizabeth Howieson Coupar, East Geelong; Marion Elizabeth Andrew, Belmont, all of Australia

[73] Assignees: Commonwealth Scientific and Industrial Research Organisation; The Australian National University, both of Australia

[21] Appl. No.: 473,301

[22] Filed: Jun. 7, 1995

Related U.S. Application Data

[63] Continuation of Ser. No. 611,112, Nov. 9, 1990, which is a continuation-in-part of Ser. No. 498,420, Mar. 26, 1990, abandoned, which is a continuation of Ser. No. 203,060, filed as PCT/AU87/00246 Jul. 31, 1987 published as WO88/0097 Nov. 2, 1988, abandoned.

[30] Foreign Application Priority Data

Aug. 1, 1986 [AU] Australia .......................... PH07212/86

[51] Int. Cl.⁶ .................................................. A61K 39/12
[52] U.S. Cl. .................................. 424/186.1; 424/188.1; 424/199.1; 435/320.1
[58] Field of Search .................................... 514/414, 816; 424/85.2, 255.1, 184.1, 88.5, 186.1, 188.1, 199.1, 93.21; 435/172.1, 172.3, 69.3, 69.1, 320.1

[56] References Cited

U.S. PATENT DOCUMENTS 4,631,191 12/1986 Dale et al. ........................... 424/186.1

FOREIGN PATENT DOCUMENTS

WO 8502200 A 5/1985 WIPO .............................. C07H 21/04

WO8502200 5/1985 WIPO .

OTHER PUBLICATIONS

Animal Pharm. 100:19 Mar. 1986.
Hu et al. Apr. 1986 Nature 320(10) 537–540.
Barinaga, M. 1994 Science vol. 266 p. 1326.
Marshall, E. 1995 Science vol. 269 pp. 1050–1055.
Crystal, R. 1995 Science vol. 270, pp. 404–410.
Jolly, D. 1994 Cancer Gene Therapy vol. 1(1) pp. 51–64.
Orkin, S.H. et al. 1995(Dec.) Report and Recommendations of the Panel to Assess the NIH Investment in Research on Gene Therapy. NIH Reports.
van Edenberg, Jun. 1989 AIDS Research and Human Retroviruses vol. 5(1) pp. 41–50.
Faney, J.L. et al. 1992 Clin. Exp. Immunol. vol. 88 pp. 1–5.
Johnson, M.I. et al 1993 Science vol. 260 pp. 1286–1293.
Animal Pharm., 100:19, Mar. 1986.
Hu et al, "Expression of AIDS virus envelope gene in recombinant vaccinia viruses", Nature 320(10):537–540, Apr. 1986.

*Primary Examiner*—Nancy Degen
*Assistant Examiner*—Irem Yucel
*Attorney, Agent, or Firm*—Bacon & Thomas

[57] ABSTRACT

A recombinant vaccine comprises a vaccine vector which incorporates a first nucleotide sequence capable of being expressed as all or a part of an antigenic polypeptide, together with a second nucleotide sequence capable of being expressed as all or a part of a lymphokine effective in enhancing the immune response to the antigenic polypeptide. The vaccine vectors include poxvirus, herpes virus or adenovirus, and the lymphokine may be an interleukin, tumour necrosis factor or gamma-interferon. The vaccine vector may express an antigenic polypeptide which is foreign to the host vector.

17 Claims, 17 Drawing Sheets

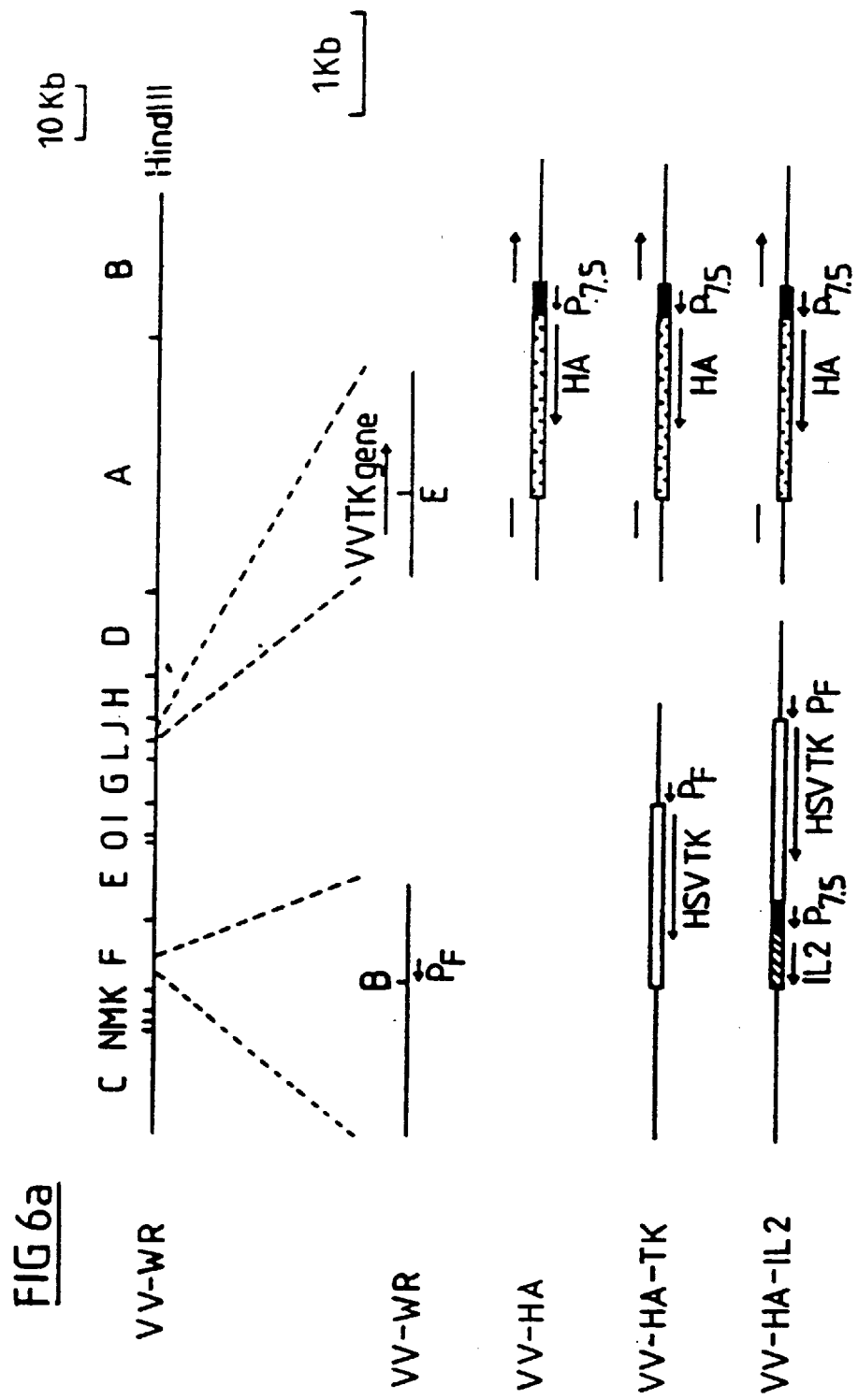

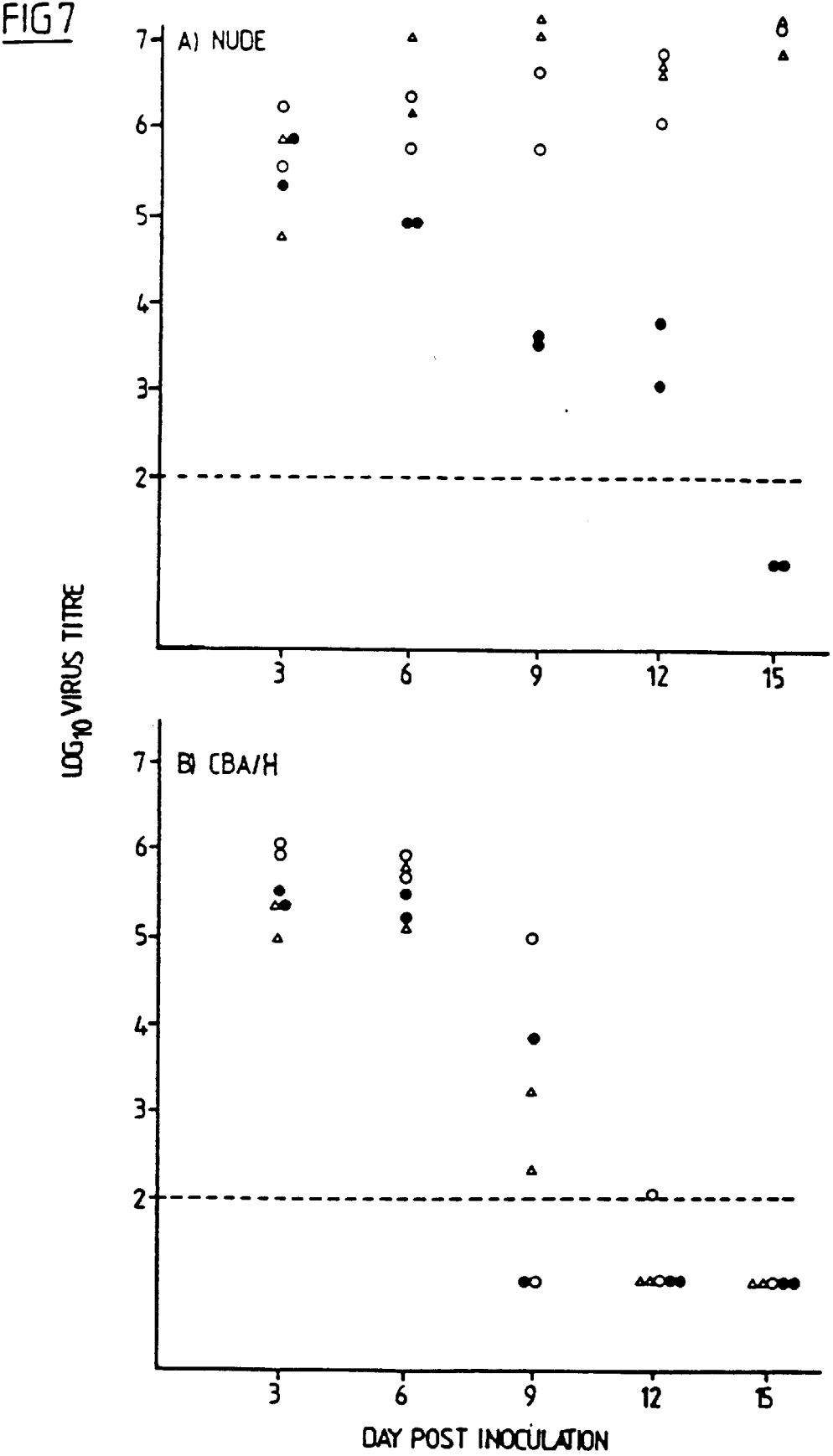

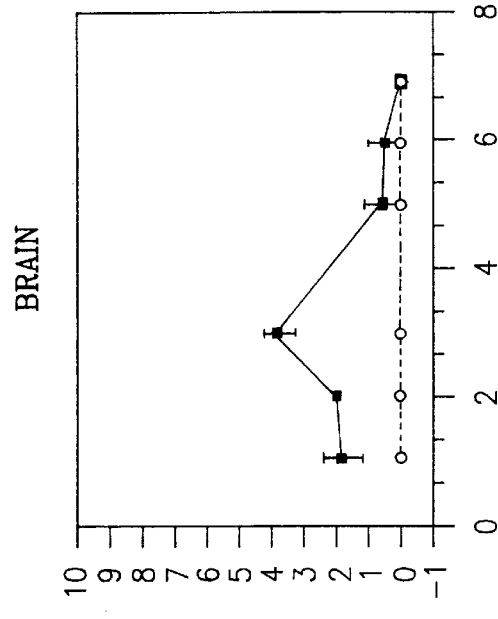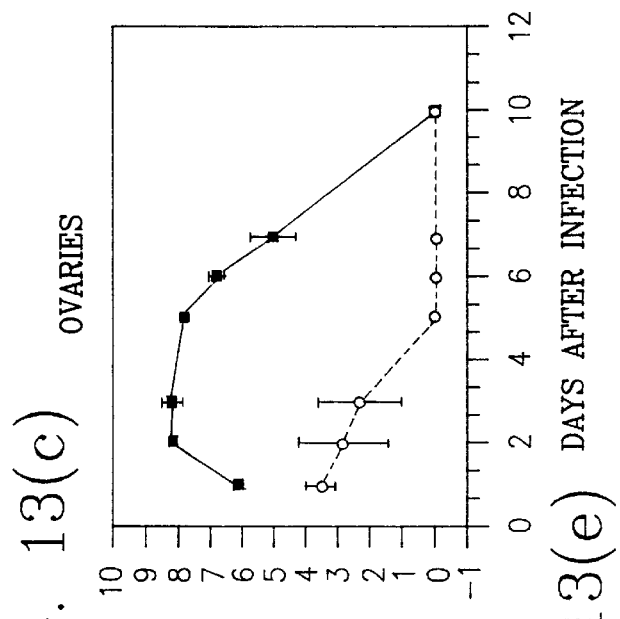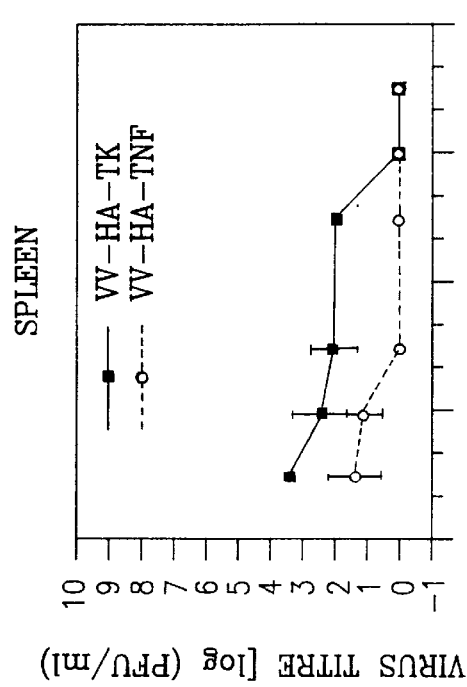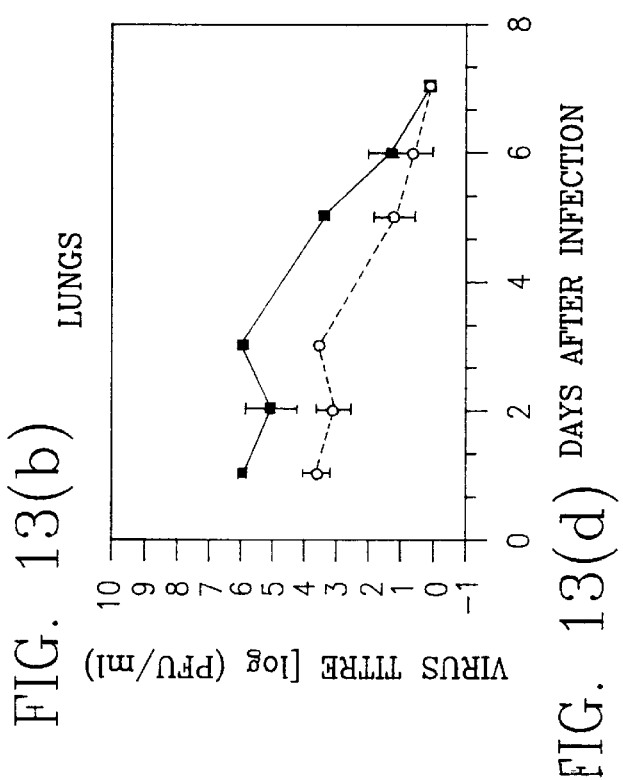
FIG. 13(b) SPLEEN
FIG. 13(c) BRAIN
FIG. 13(d) LUNGS
FIG. 13(e) OVARIES

RECOMBINANT VACCINE

CROSS REFERENCE TO RELATED APPLICATIONS

This specification is a continuation of application Ser. No. 07/611,112, filed on Nov. 9, 1990; which is a continuation-in-part of application Ser. No. 07/498,420 filed on Mar. 26, 1990, now abandoned; which is a continuation of application Ser. No. 07/203,060, filed on Jun. 1, 1998, now abandoned; which is a continuation application of international application Ser. No. PCT/AU87/00246, filed on Jul. 31, 1997, published as WO88/0097 nov. 2, 1988, now abandoned.

BACKGROUND TO THE INVENTION

This invention concerns new vaccines developed using recombinant DNA technology to provide useful immune responses in circumstances where traditional vaccines may not be sufficiently effective.

Many existing live or killed vaccines are not without disadvantages, often significant, in respect of, for example, high production costs, poor response, low response to poorly immunogenic antigens, instability and a requirement for adjuvants. Furthermore, alternative vaccine preparations based on agents such as purified proteins or synthetic peptide antigens frequently offer only poor protection. In response to these problems, attention has turned to the development of vaccines in which recombinant DNA methods have been used to introduce antigens to which immunity is required, into carrier viruses such as vaccinia.

The advantage of the recombinant DNA approach is that an infectious recombinant virus simultaneously synthesises the foreign polypeptide and viral antigen, which can then be delivered to a host immune system as a superficial skin lesion. Vaccinia viruses have, for example, been modified for expression of the genes for hepatitis B, human immunodeficiency virus, influenza and malaria antigens; the construction of recombinant viruses carrying other antigens of medical or veterinary importance is under investigation.

In some instances, however, the immune response of recombinant vaccines may be of limited nature and magnitude. Thus, while peripheral immunisation with vaccinia-influenza recombinants provides good protection against lower respiratory tract infection, it fails to induce immunity in the upper respiratory tract. On the other hand, peripheral immunisation with recombinant vaccines may prove ineffective when local rather than systemic immunity is required, as in say the gastro-intestinal tract.

There have been various attempts to remedy these deficiencies, including expression of vaccine antigens through viruses having stronger promoters, such as poxvirus, but to date these have not met with significant success. The present invention provides an effective means for enhancing the immune response to the specific foreign antigenic polypeptides of recombinant vaccines.

The immune system is regulated in part by molecules, known as lymphokines, which are released by lymphocytes and help or modify the functions of other classes of lymphocytes. The present invention is based on a recognition that the expression of appropriate lymphokines from recombinant bacterial or viral vaccines can boost and/or modify the immune response to viral, bacterial or co-expressed foreign antigenic polypeptides.

SUMMARY OF THE INVENTION

Accordingly, in its broadest aspect, this invention provides a recombinant vaccine comprising a vaccine vector which incorporates a first nucleotide sequence capable of being expressed as an antigenic polypeptide, together with a second nucleotide sequence capable of being expressed as all or an active part of a lymphokine effective in enhancing or modifying the immune response to the antigenic polypeptide.

In accordance with one embodiment of this invention, the first nucleotide sequence capable of being expressed as an antigenic polypeptide may be a "native" sequence of the host vector itself, for example vaccinia or herpes virus. In this embodiment, administration of the vaccine of this invention provides augmentation and/or selective induction of the immune response to the "native" antigenic polypeptide. In other words, the inclusion of the lymphokine in the recombinant vaccine may substantially modify the immunogenicity of the host vector. Where the host vector is a virus such as vaccinia virus, the system offers the advantage that the lymphokine is continuously produced at the site of virus replication throughout the immune response, with the effect in some instances of dramatic modification of the pathogenicity of the vaccinia virus, and in other cases altering the immune response to the viral antigens.

In another embodiment, the vaccine vector incorporates a nucleotide sequence capable of being expressed as an antigenic polypeptide which is foreign or heterologous to the host vector. In this embodiment, administration of the vaccine to an individual will result in augmentation and/or selective induction of the immune response of the individual to both antigenic polypeptide of the host vector and to co-expressed foreign or heterologous antigenic polypeptide. As discussed below, the co-expression of the lymphokine with the antigenic polypeptide(s) ensures that on administration of the vaccine the lymphokine and antigenic polypeptide(s) are delivered together at the same time and at the same site, giving an improved immune response to the antigenic polypeptide(s).

In another aspect, the present invention provides a method for producing an immune response in a human or animal, in particular an immunodeficient or immunosuppressed human or animal, which comprises the step of administering to the human or animal a recombinant vaccine as broadly described above.

BRIEF DESCRIPTION OF THE DRAWINGS

FIG. 6a depicts the genomic configuration of VV recombinants.

FIG. 7 shows the growth of vaccinia virus recombinants in the foot pads of athymic Swiss outbred nude mice and athymic CBA/H mice.

FIGS. 13(b)–13(e) are a group of graphs which show the growth kinetics of VV recombinants as determined by samples taken from selected organs of mice which were injected with VV-HA-TNF or VV-HA-TK.

Figure 1:
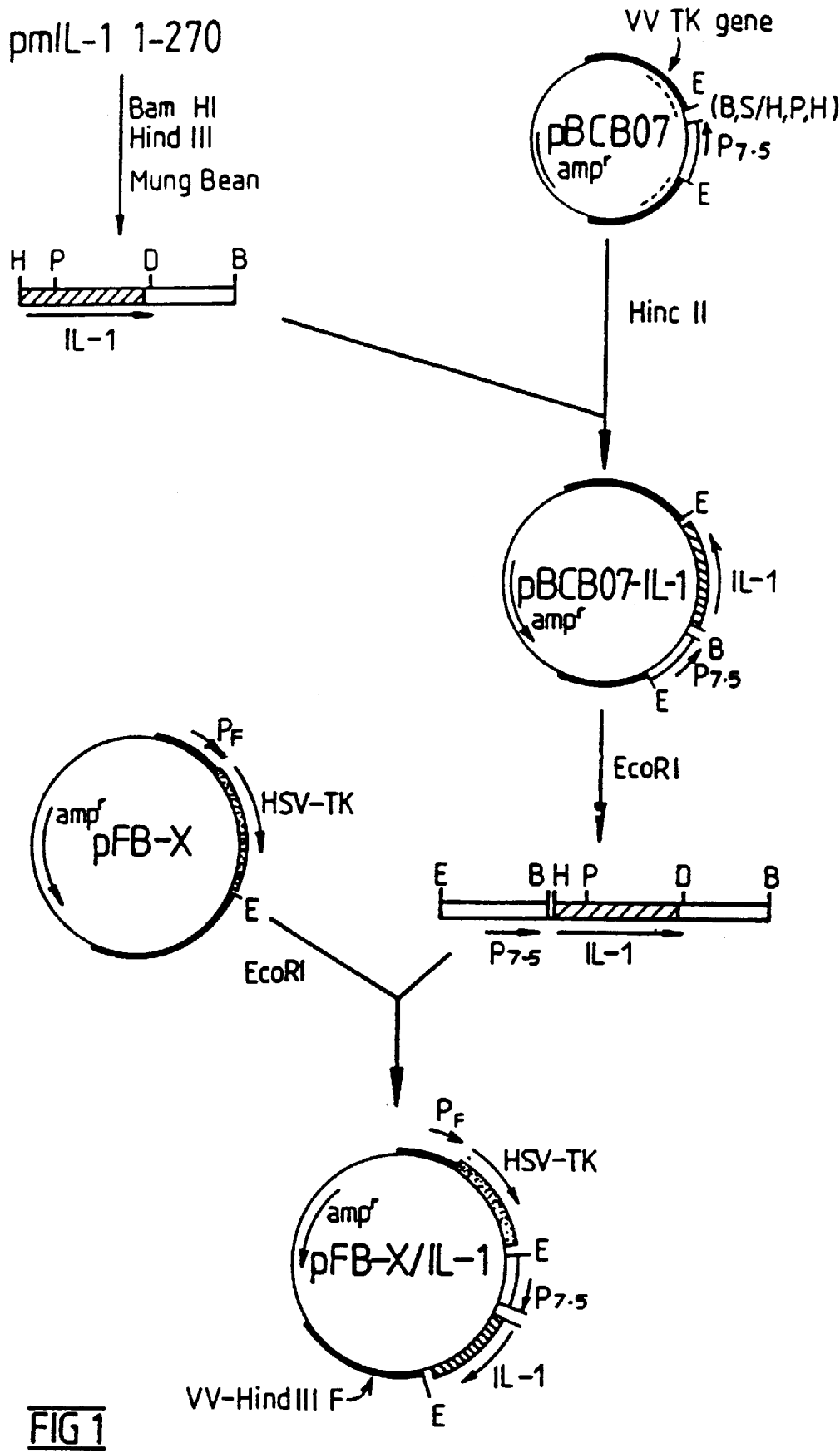
FIG. 1 is a flow chart which depicts the construction of vaccinia virus expressing IL-1.

It will be appreciated from the broad description set out above that the present invention has particular application in the augmentation of immune responses in immunodeficient or immunosuppressed individuals. In one particularly important aspect of this invention, there is provided a recombinant vaccine for use in the treatment or prophylaxis of immunodeficient or immunosuppressed individuals infected with the human immunodeficiency virus (HIV), which comprises a vaccine vector which incorporates a nucleotide sequence capable of being expressed as an antigenic polypeptide derived from the human immunodeficiency virus (HIV), together with a second nucleotide sequence capable of being expressed as all or an active part a lymphokine effective in enhancing or modifying the immune response of the individual to the HIV antigenic polypeptide.

The lymphokines which may be expressed in vaccines according to this invention include those designated interleukin-1 (IL-1), interleukin-2 (IL-2), interleukin-3 (IL-3), interleukin-4 (IL-4), interleukin-5 (IL-5), tumour necrosis factor (TNF), and γ-interferon (γ-IFN).

Interleukin-1 is a peptide hormone largely. produced by activated macrophages. IL-1 modulates the proliferation, maturation and functional activation of a broad spectrum of cell types (1–3) and plays a major role in the initiation and amplification of immune and inflammatory responses through its action on these diverse cell populations (4). The gene for murine (5) and human (6) IL-1 has been cloned and expressed in E. coli.

Interleukin-2 is a lymphokine produced by helper T cells and is active in controlling the magnitude and type of the immune response (7). Other functions have also been ascribed to IL-2 including the activation of NK cells (8) and the stimulation of cell division in large granular lymphocytes and B cells (9). Numerous studies in mice and humans have demonstrated that deficient immune responsiveness both in vivo and in vitro can be augmented by IL-2. For example, exogenous IL-2 can restore the immune response in cyclophosphamide-induced immunosuppressed mice (10) and athymic (nude) mice (11). Furthermore, IL-2 can restore responsiveness of lymphocytes from patients with various immunodeficiency states such as leprosy and cancer (12). IL-2 has also been used for the treatment of cancer (13). The gene for murine (14) and human (15) IL-2 has been cloned and sequenced.

Interleukin-3 is a hormone-like glycoprotein produced by lectin or antigen activated T lymphocytes and possibly other cells within the bone marrow. The hormone stimulates the growth and differentiation of haematopoietic progenitor cells and multipotential stem cells and has been described under a variety of names, among them multi-colony stimulating factor, and haematopoietic growth factor (16). The gene for mouse IL-3 has been cloned and sequenced (17).

Interleukin-4 is a T cell derived factor that acts as an induction factor on resting B cells, as a B cell differentiation factor and as a B cell growth factor (18). The factor also stimulates T cells and acts as a mast cell growth factor (18). The gene for murine (19) and human (20) IL-4 has been isolated and sequenced.

γ-interferon is also a T cell derived molecule which has profound effects on the immune response. The molecule promotes the production of immunoglobulin by activated B cells stimulated with interleukin-2. γ-interferon also increases the expression of histocompatibility antigens on cells which associate with viral antigens to stimulate cytotoxic T cells. The gene for human γ-interferon has been isolated and sequenced (21).

Other lymphokines including interleukin-5 and tumour necrosis factor are also well known. Thus, interleukin-5 (IL-5) stimulates the production of several immunoglobulin classes, however its major function may be to promote IgA synthesis, thereby playing a crucial role in regulating mucosal immune responses. The mechanism by which IL-5 acts is unclear, although in vitro data indicate that it promotes terminal B cell differentiation.

The co-expression of a lymphokine such as IL-2 and an antigenic polypeptide by a recombinant vaccine (such as a recombinant virus vaccine) ensures that they are produced together by the same infected cells in a very localised area. This can be expected to lead to an elevation and acceleration of response to the virus vector component of the vaccine, e.g. vaccinia virus, with attendant benefits such as a reduction in the risks of complication associated with the use of vaccinia virus in normal individuals, and to those unidentifiable individuals who react adversely to vaccinia virus. Also, where there are immunological defects, as in the case of patients suffering from AIDS, leprosy or cytomegalovirus infection, co-expression of lymphokine could be instrumental in overcoming the defects to allow a normal response to the antigenic polypeptide and/or vector virus.

Furthermore, it is anticipated that the present invention will prevent or at least minimise the complications such as generalised vaccinia that can occur when vaccine is administered inadvertently to immunodeficient recipients (32).

Further, cancer patients often show a negligible or poor immunological response to the cancer antigens. It may be possible to enhance those responses to useful levels by taking cancer cells from the hosts, infecting them with, say, vaccinia virus/IL-2 recombinants, and returning them to the patient. To guard against generalised vaccinia infection or spread of the cancer cells it may, of course, be advisable to inactivate the recombinant-infected cancer cells prior to return to the patient.

Other lymphokines (e.g. IL-1, IL-3, IL-4, IL-5, TNF and γ-IFN), are involved in the control and augmentation of responses in other parts of the immune system including granulocyte-macrophage lineage, eosinophil differentiation and mucosal immunity. Construction of co-expressive vaccines will enable advantage to be taken of these specific modes of activity. Thus, as they are believed to have a role in the generation of protective responses at mucosal surfaces, such as in the gut, which promote expulsion of and immunity to parasites, a vaccine co-expressing IL-3 (or other lymphokine) with a helminth or other parasite antigenic polypeptide would be expected to give rise to enhanced immunity compared to that from the parasite antigen alone.

Whilst a specific example of co-expression of the influenza haemagglutinin (HA) is described in detail herein, it will be appreciated that the present invention may be applied for the co-expression of other foreign or heterologous antigens including hepatitis virus, herpes simplex virus, Epstein-Barr virus and human immunodeficiency virus (HIV) antigens, as well as malaria antigens. Prior work has demonstrated that protection may be obtained against influenza virus following immunisation with a recombinant vaccinia virus that expresses influenza haemagglutinin (34,35). However this prior work does not teach or suggest the co-expression of the haemagglutinin and a lymphokine in the same recombinant vaccinia virus, or the advantages arising from such co-expression as disclosed herein.

As previously described, vaccinia virus has been used as a vaccine vector to deliver antigens of unrelated infectious agents such as hepatitis B virus (22) and human immunodeficiency virus (23). The expression of an inserted gene in vaccinia virus requires that the gene be placed next to a vaccinia promoter. The promoter usually used is designated p7.5 (22). This chimeric gene is then placed next to a DNA fragment of vaccinia virus taken from a non-essential region of the virus. Insertion into infectious virus is by homologous recombination in which a marker rescue is used to select for virus recombinants. By way of example, the marker rescue can be either selection for thymidine kinase negative (TK⁻) virus in which the foreign gene has been inserted and thereby inactivating the TK gene; or by selecting for TK⁺ virus in which the foreign gene is flanked by the herpes simplex TK gene. The latter is generally used to construct double recombinants that is, viruses expressing two foreign genes.

The expression of lymphokine genes in vaccinia virus may be detailed as two stages; the first is to create a plasmid in which the lymphokine is under the control of a vaccinia promoter 7.5 and downstream from a thymidine kinase (HSV) gene. This plasmid is then used to transfect TK- cells previously infected with a TK⁻ vaccinia virus expressing another foreign gene. TK⁺ recombinant virus is then selected by culturing cells in the presence of methotrexate.

Although this invention has primarily been described with reference to vaccinia virus as the vaccine vector, it is to be understood that the inventive concept resides in co-expression of an antigenic polypeptide and lymphokine, and this concept may be realised using other vaccine vectors, such as other poxvirus, herpes virus, adenovirus or bacteria.

It is also to be understood that the invention is not limited by application to man or other species specifically mentioned herein, but may find application in a wide range of animal species.

Methods for construction and testing of recombinant vaccines according to this invention will be well known to those skilled in the art, however, for better understanding of the invention some typical techniques will now be described. Standard procedures for endonuclease digestion, ligation and electrophoresis were carried out in accordance with the manufacturer's or supplier's instructions. Standard techniques are not described in detail and will be well understood by persons skilled in the art.

EXAMPLE 1

Plasmids containing IL-1, IL-2, IL-3, IL-4 and γ-interferon are shown in FIGS. 1–5. Plasmids pmIL-1 1.270, pcD-IL-3, pcD-HuIL-2, pcD-IL-4 and pcD-HuγINF were obtained from DNAX Research Institute. The excised coding sequence is shown as the hatched bar. It is necessary to use different restriction endonucleases to create suitable termini for insertion into plasmid; these are detailed in the respective diagrams. pBCB07 (25,38) contains the vaccinia 7.5K promoter, pFB-X (27) contains the HSV TK coding sequence (stippled) inserted at a BamH1 site downstream from a promoter in the vaccinia HindIII region. The recombinant plasmids pFB-X/IL1, pFB-X/IL2, pFB-X/IL3, pFB-X/IL4, pRB-X/γ-interferon contain HSV-TK and lymphokine genes 3' to different vaccinia virus promoters and with flanking sequences derived from the HindIII F fragment of vaccinia virus. The orientations of genes and promoters are shown with arrows, vaccinia virus sequences with solid lines and plasmid DNA by thin lines. The pFB-plasmids with inserted lymphokine genes are used to transfect 143B (TK⁻) cells previously infected with a TK⁻ vaccinia virus according to conditions previously described (24). The site of insertion of HSV TK and lymphokine coding sequences and transposed vaccinia promoters in the vaccinia virus genome are shown in FIG. 6. Vaccinia-virus WR strain HindIII restriction fragments are shown in the top line. Lower lines show in expanded form the DNA configurations at insertion sites in the HindIII J and F fragments. Orientations of coding sequences and promoter sequences are shown with arrows.

EXAMPLE 2

This example describes the construction of a recombinant vaccinia virus (VV) expressing murine IL2 and the effect of the lymphokine on virus growth and immunogenicity.

Figure 6B:
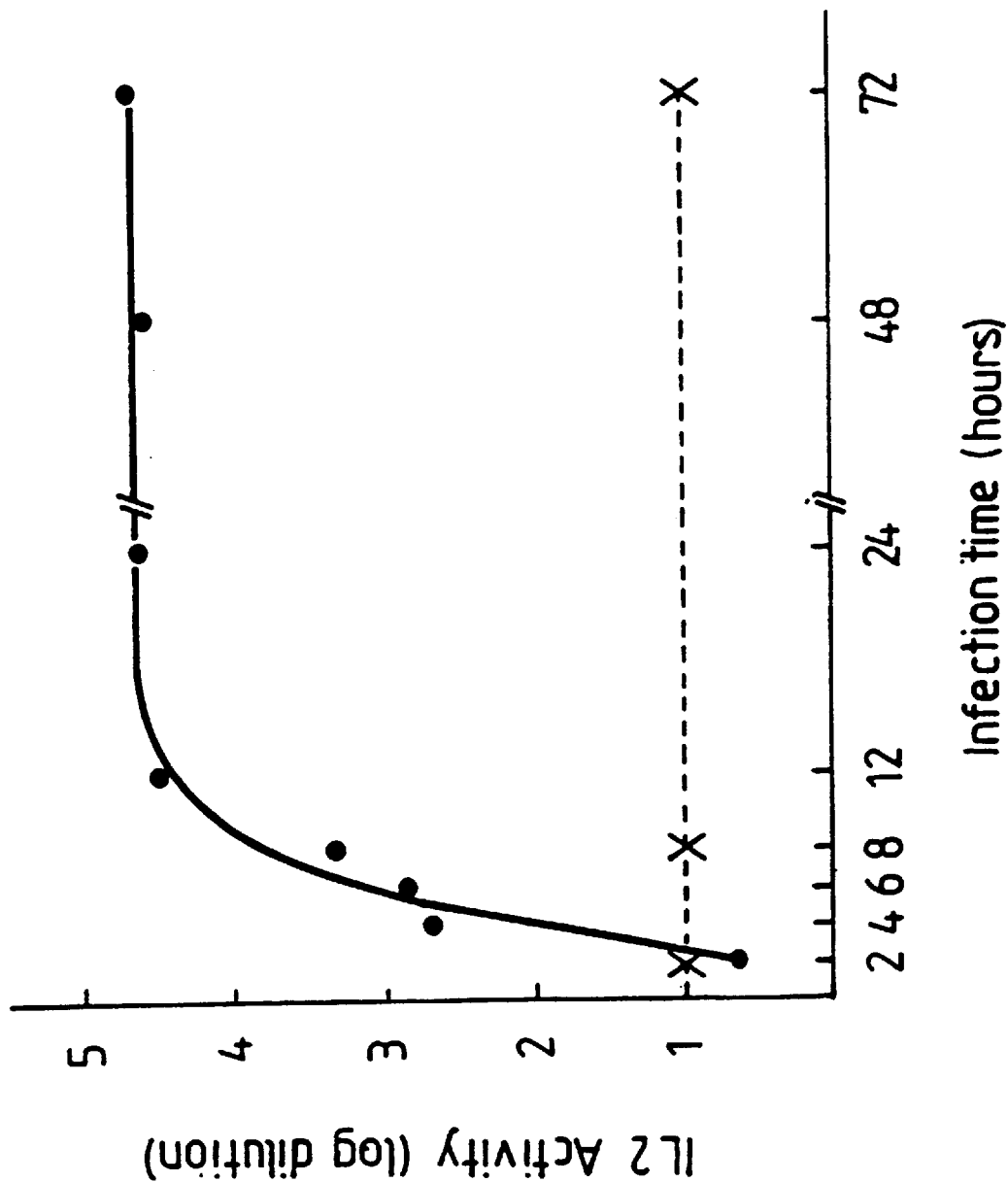
FIG. 6b is a graph which shows the production of IL2 production by VV-HA IL2-infected human 143B cells over a period of time.

FIGS. 6A and 6B show:
(a) Genomic configuration of VV recombinants. A HindIII map of VV WR strain is shown with insertion points at EcoRI (E) and BamHI (B) sites in the J and F fragments respectively. Arrows indicate orientations of VV TK gene, VV promoters and inserted influenza HA, HSV TK and murine IL2 coding sequences.
(b) Time course of IL2 production by VV-HA IL2-infected human 143B cells. IL2 activity in VV-HA-IL2-infected supernatants, circles and solid line; VV-HA or uninfected cell supernatants, crosses and dotted line.

FIGS. 7A and 7B show the growth of vaccinia virus recombinants in the foot pads of athymic Swiss outbred nude mice (a) and athymic CBA/H mice (b). $2 \times 10^7$ PFU of VV-HA (triangles), VV-HA-TK (open circles) or VV-HA-IL2 (closed circles) were injected subcutaneously in 20 μl into hind foot pads which were assayed for infectious virus on 143B cells on the indicated days. Points represent the titres of infectious virus present in individual mice.

As shown schematically in FIG. 6a, cDNA encoding murine IL2 (14) was inserted into the HindIII F region of a VV recombinant, VV-HA (26), which already expressed the influenza haemagglutinin (HA). The IL2 recombinant virus, VV-HA-IL2, coexpressed HA and IL2 using the same VV 7.5 Kd promoter but from separate sites in the viral genome. Since the herpes simplex virus (HSV) thymidine kinase (TK) gene was used as a selectable marker for virus construction a control virus VV-HA-TK, expressing HSV TK but not IL2 was constructed. Significant levels of biologically active IL2 were detected in supernatants from human 143B cells infected with VV-HA-IL2 within 4 hours and reached maximum activity around 12 hours (FIG. 6b).

Athymic nude mice were inoculated into the right hind footpad with VV-HA-IL2 or control virus (VV-HA-TK). VV-HA-IL2 induced a mild swelling in the foot which resolved after several days; in contrast VV-HA-TK produced a severe necrotic lesion that remained unresolved for 30 days. After this time, high titres of virus ($6 \times 10^5$–$1.5 \times 10^7$ PFU) were recovered from the feet of the VV-HA-TK inoculated mice but not from mice given VV-HA-IL2. This suggested that the IL2 produced by the recombinant virus enabled immunodeficient mice to control the virus infection. The kinetics of viral clearance from the feet of CBA/H mice were not significantly different for VV-HA-TK and VV-HA-IL2 (FIG. 7a). However, in nude mice, although titres of both VV-HA-TK and VV-HA-IL2 were high at day 3, indicating comparable rates of replication, VV-HA-IL2 was cleared by day 15 when no virus was detected in the feet. Titres of VV-HA-TK still remained high at day 15 (FIG. 7b). Furthermore, when nude mice were injected intravenously (i.v.) with $10^6$ PFU of VV-HA-IL2 or VV-HA-TK, mice given VV-HA-IL2 appeared unaffected by the virus whereas all mice given VV-HA-TK were moribund by day 15. Consistent with this result infectious virus was recovered from spleens and lungs of VV-HA-TK- but not VV-HA-IL2-infected mice (Table 1).

TABLE 1

Vaccinia Virus recovered from Lungs and Spleen

| Mouse Strain | Organ | Log · 10 VV-HA-TK | Log · 10 VV-HA-IL2 |
|---|---|---|---|
| CBA/H | Lung | <2.0 | <2.0 |
|  | Spleen | <2.0 | <2.0 |
| Outbred | Lung | 4.91 ± 0.27 | <2.0 |
| Nude | Spleen | 3.64 ± 0.11 | <2.0 |

Lungs and spleens were collected from 3–4 mice/group 11 days post i.v. inoculation with $10^6$ PFU of the indicated virus.

Methods (a) Murine IL-2 cDNA was subcloned from pcD-IL-2, (14) generously provided by Dr K. I. Arai, DNAX Research Institute, Palo Alto, Calif. VV-HA-IL2 and VV-HA-TK were constructed by insertion of the HSV TK gene plus a chimeric promoter-IL2 fragment or alone, into the HindIII F region of the recombinant VV-HA (previously described as VV-PR8-HA6) (26) using plasmids as described in Example 1 and appropriate selection protocols (27, 28).

(b) 143B cells $2 \times 10^6$ were infected with VV-HA-IL2 at 5 PFU/cell. The supernatants (1.5 ml), harvested at the time points indicated, were assayed for IL2 activity using CTLL-2 cells (29) and the colorimetric method for cell growth of Mosmann (30). The results are presented as the log dilution of supernate producing 50% of maximum proliferation in the cell cultures.

EXAMPLE 3

Figure 2:
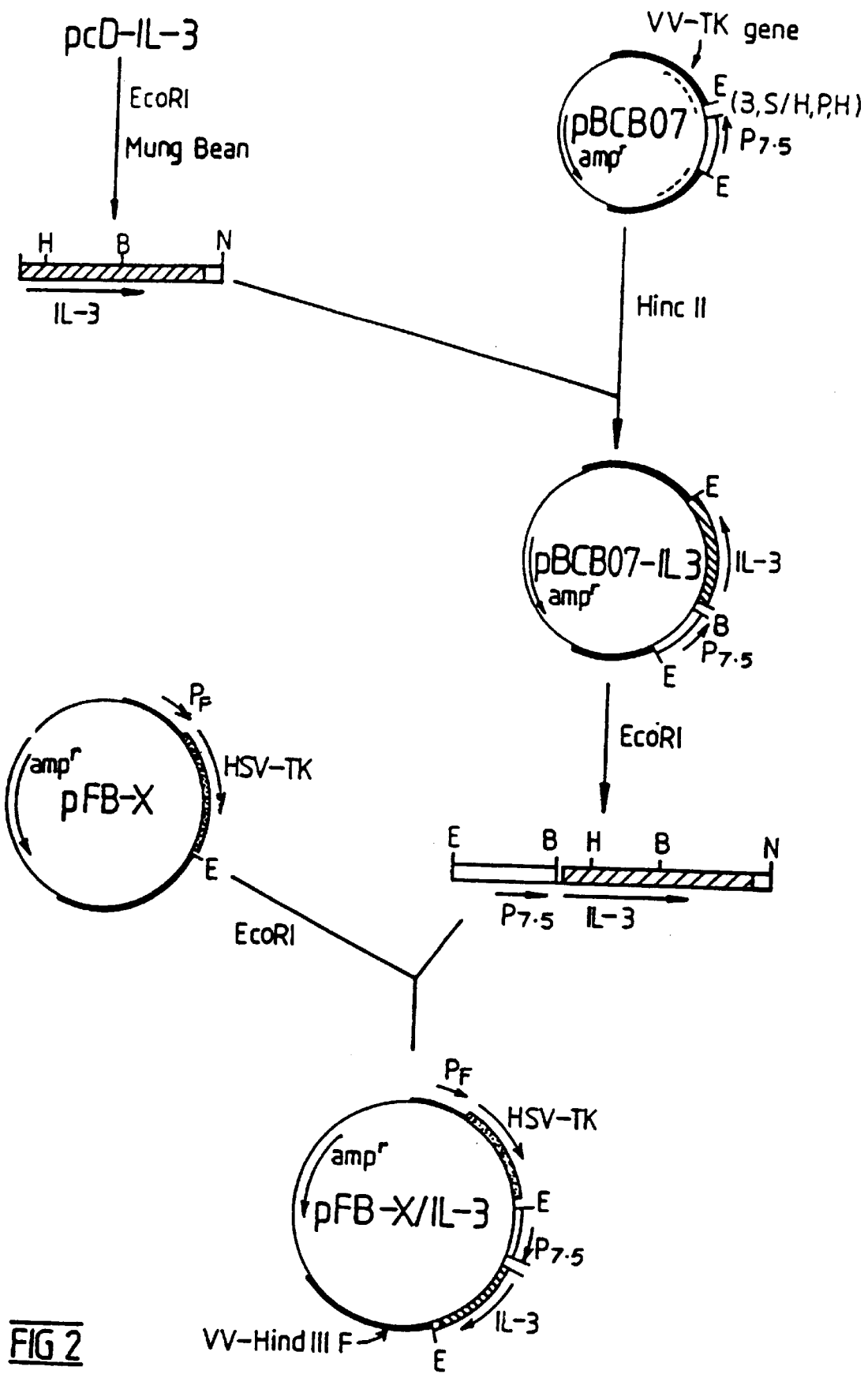
FIG. 2 is a flow chart which depicts construction of a vaccinia virus expressing IL-3.
Figure 3:
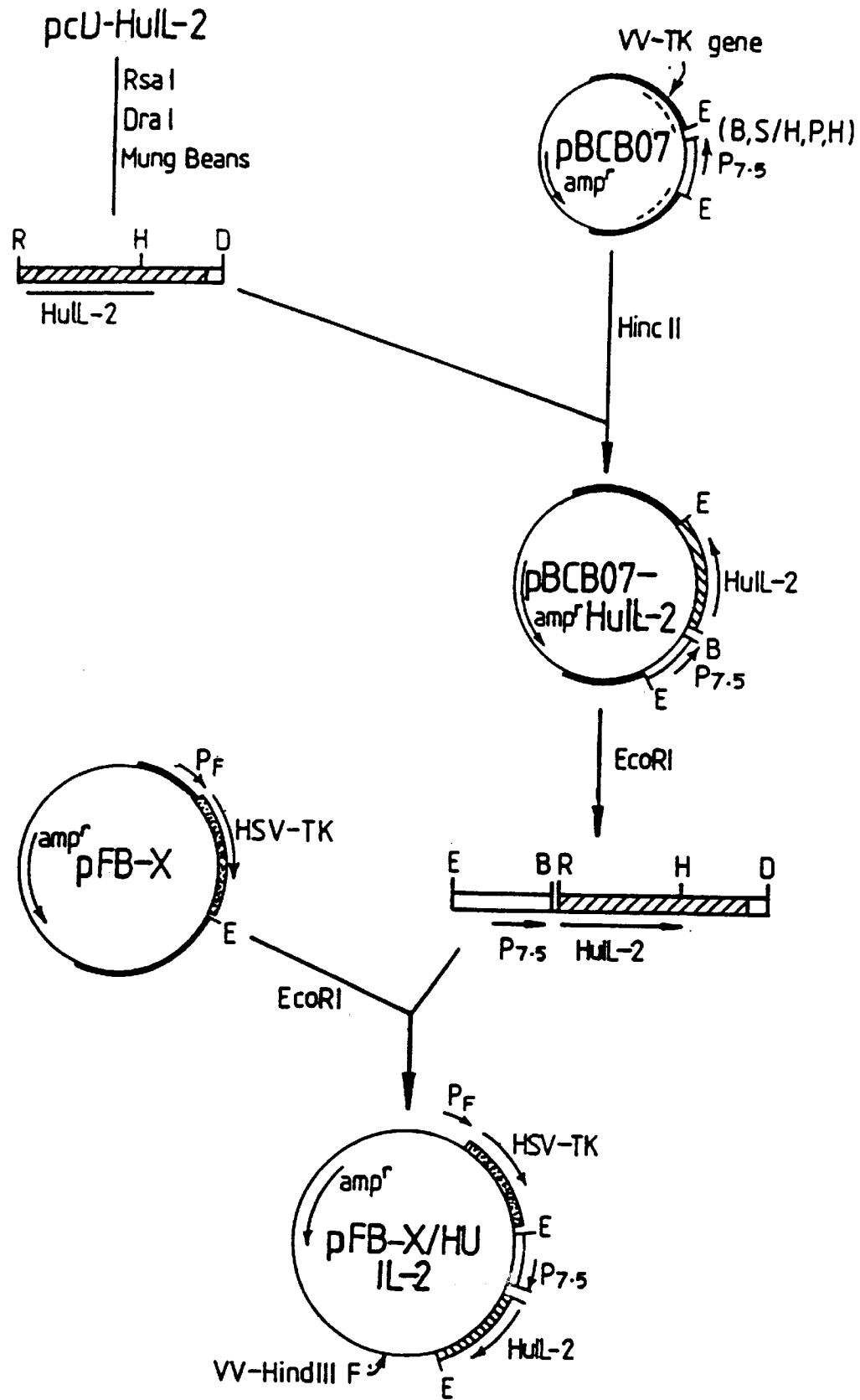
FIG. 3 is a flow chart which depicts construction of a vaccinia virus expressing HuIL-2.
Figure 4:
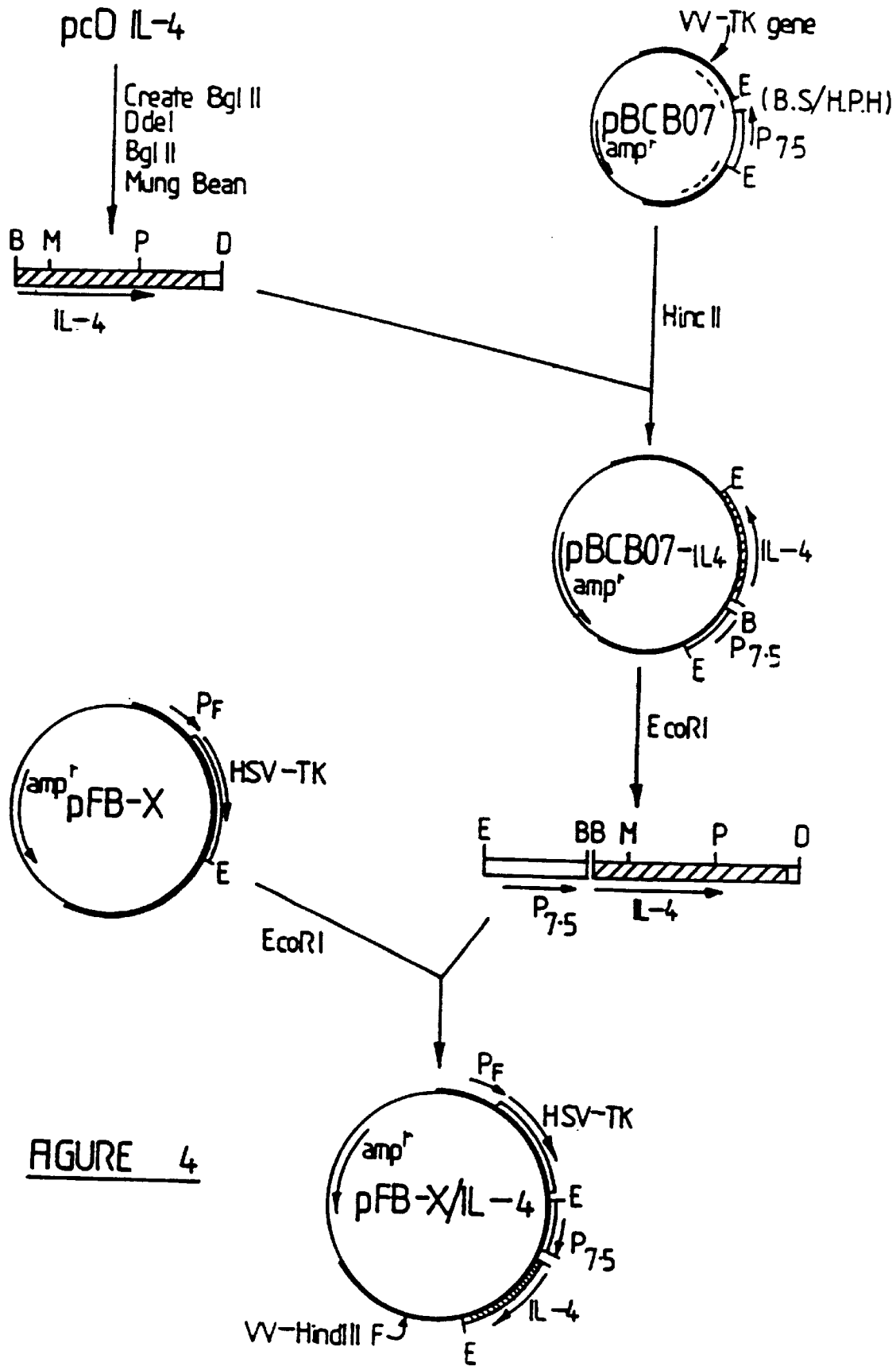
FIG. 4 is a flow chart which depicts construction of a vaccinia virus expressing IL-4.
Figure 5:
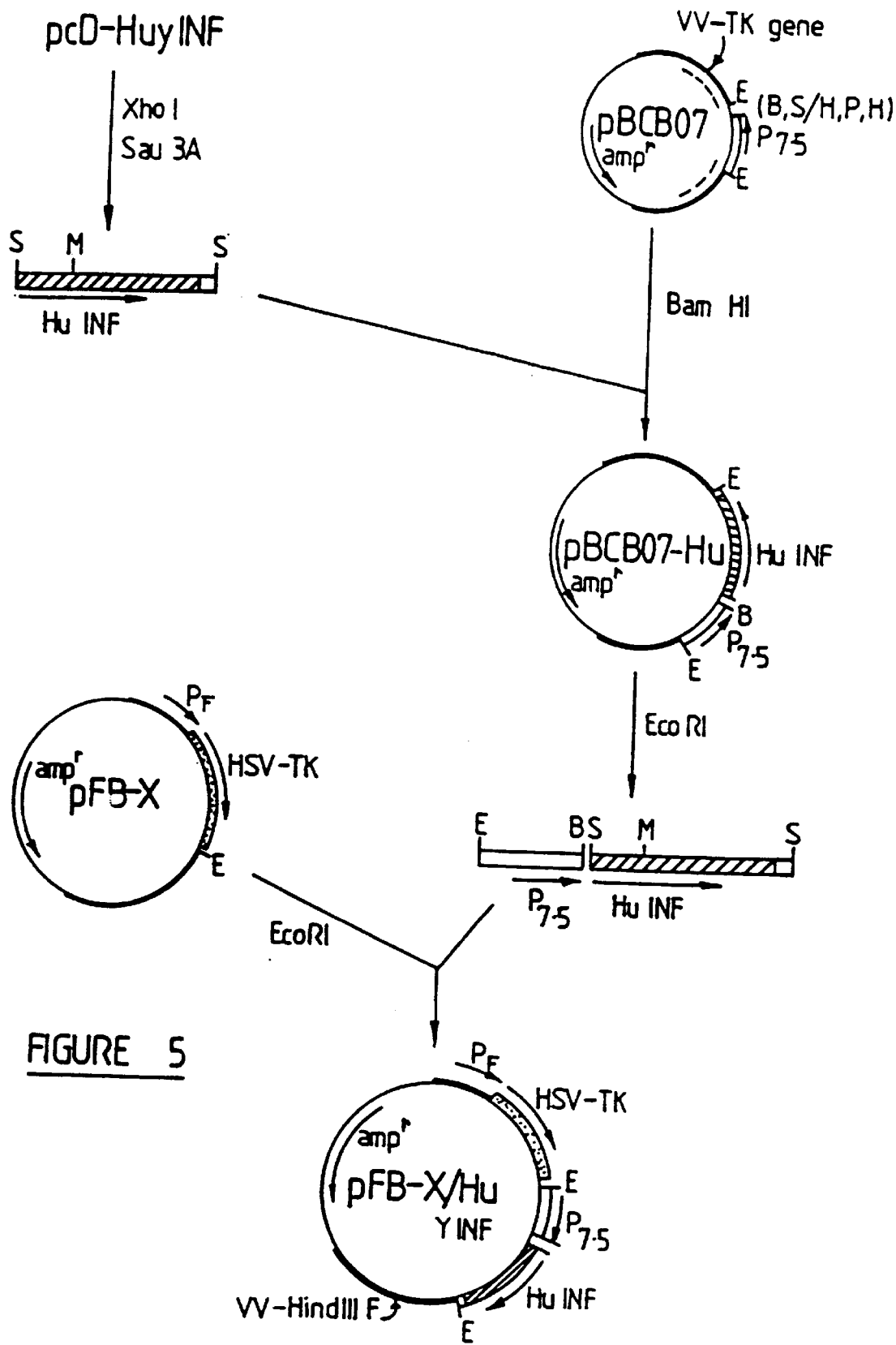
FIG. 5 is a flow chart which depicts construction of a vaccinia virus expressing Hu INF.

A vaccinia virus expressing IL-3 was constructed as shown in FIG. 2, using the methods described in Example 1.

Irradiated mice (650 Rads) injected with vaccinia virus ($10^6$ PFU intravenously) expressing IL-3 (VV-IL-3) show a reconstituted haematopoietic system within seven days. Spleen cell counts are given below:

| | Spleen Cell Number | |
|---|---|---|
| | VV-IL-3 | NIL |
| 4 days | $3 \times 10^7$ | $5 \times 10^6$ |
| 7 days | $2 \times 10^8$ | $2 \times 10^6$ |
| 10 days | $1 \times 10^8$ | $3 \times 10^6$ |

In addition, the injection of vaccinia virus expressing IL-3 (VV-IL-3) protects mice against the lethal effects of irradiation, as follows:

| | Deaths | |
|---|---|---|
| Irradiation Dose | VV-IL-3 | NIL |
| 950 Rads | 0/6 | 6/6 |

EXAMPLE 4

This example describes the construction of a recombinant adenovirus expressing interleukin genes.

The starting virus for the adenovirus construct is adenovirus type 5 deletion mutant d1 327 that lacks the Xba fragment from 78.5 map units to 84.7 map units in early region 3 (31). This deletion mutant allows the insertion of DNA without exceeding the amount of DNA that can be included in the virus particle. The removal of the E3 region also prevents production of a virus protein that complexes with the major histocompatibility heavy chain protein and reduces the cell-mediated immune response to the virus. The Bam fragment from 60 map units to the right hand end of the viral DNA is cloned in plasmid. The plasmid DNA is cut downstream of the E3 promoter with a suitable restriction enzyme and the interleukin gene inserted in place of the original E3 gene, under the control of the natural E3 promoter. The resulting plasmid containing the interleukin gene in the 60 to 100 map unit fragment of d1 327 is cut with the appropriate restriction enzyme to separate viral and plasmid DNA and transfected into cells together with the overlapping EcoR1 A fragment (0 to 76 map units) of wild type virus. Recombination between the two overlapping DNA fragments will reconstitute viable adenovirus in which the E3 gene is replaced by the interleukin gene.

EXAMPLE 5

Figure 8:
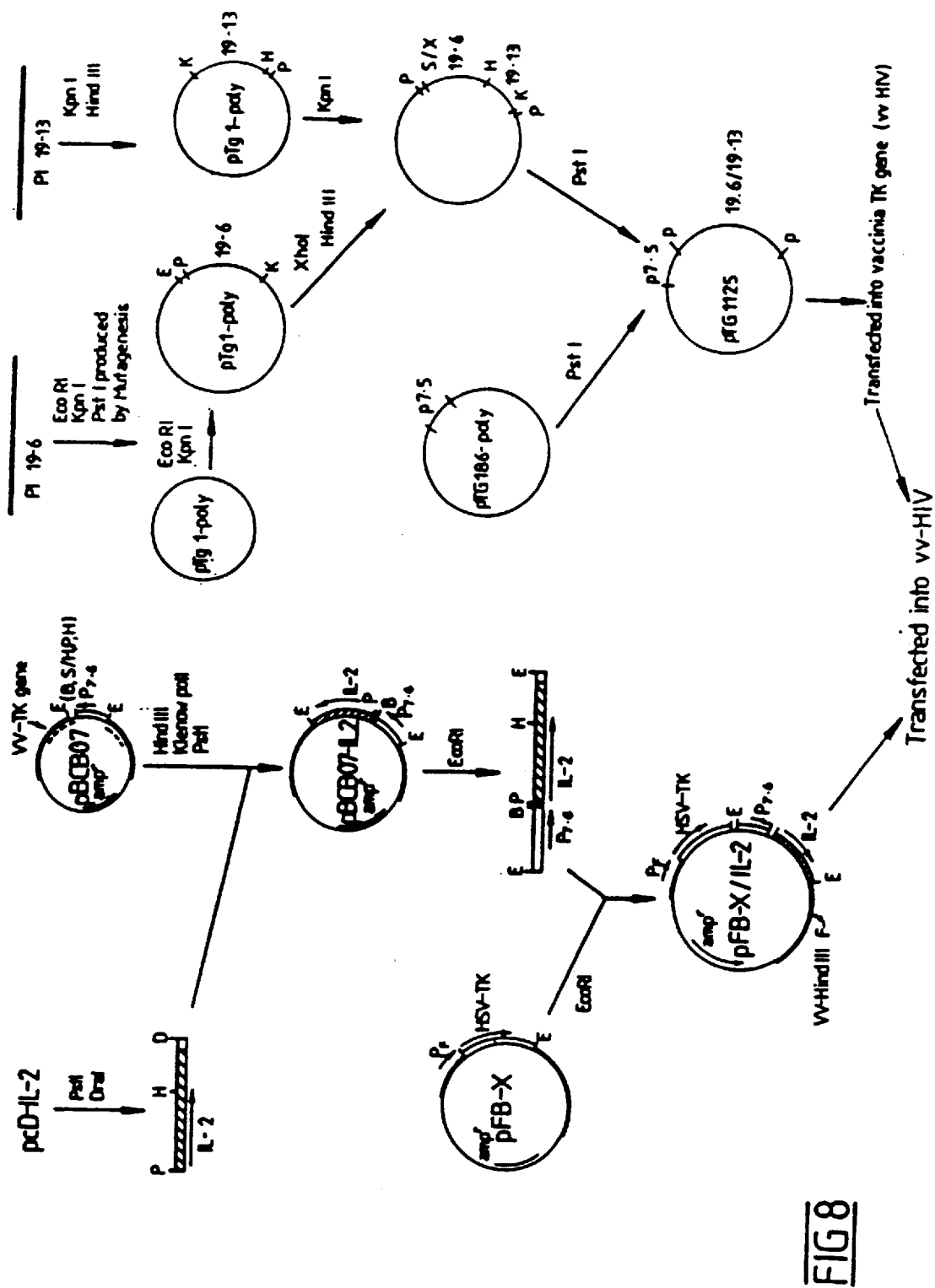
FIG. 8 is a flow chart which depicts the construction of human immunodeficiency virus IL-2 recombinant vaccinia virus in accordance with the present invention.

FIG. 8 outlines the construction of human immunodeficiency virus IL-2 recombinant vaccinia virus in accordance with the present invention. pFB-X/IL-2 is constructed as shown using the methods described in Example 1. The construction of pTG1125 is as previously described (33). As shown in FIG. 8, plasmid pTG 1125 is transfected into the vaccinia TK gene to give recombinant vaccinia virus VV-HIV, and the plasmid pFB-X/IL-2 is then transfected into VV-HIV to give the desired recombinant vaccinia virus in accordance with this invention.

EXAMPLE 6

(a) This example demonstrates protection from influenza virus A/PR/8/34 in nude mice recovered from infection with VV-HA-IL2.

Figure 9:
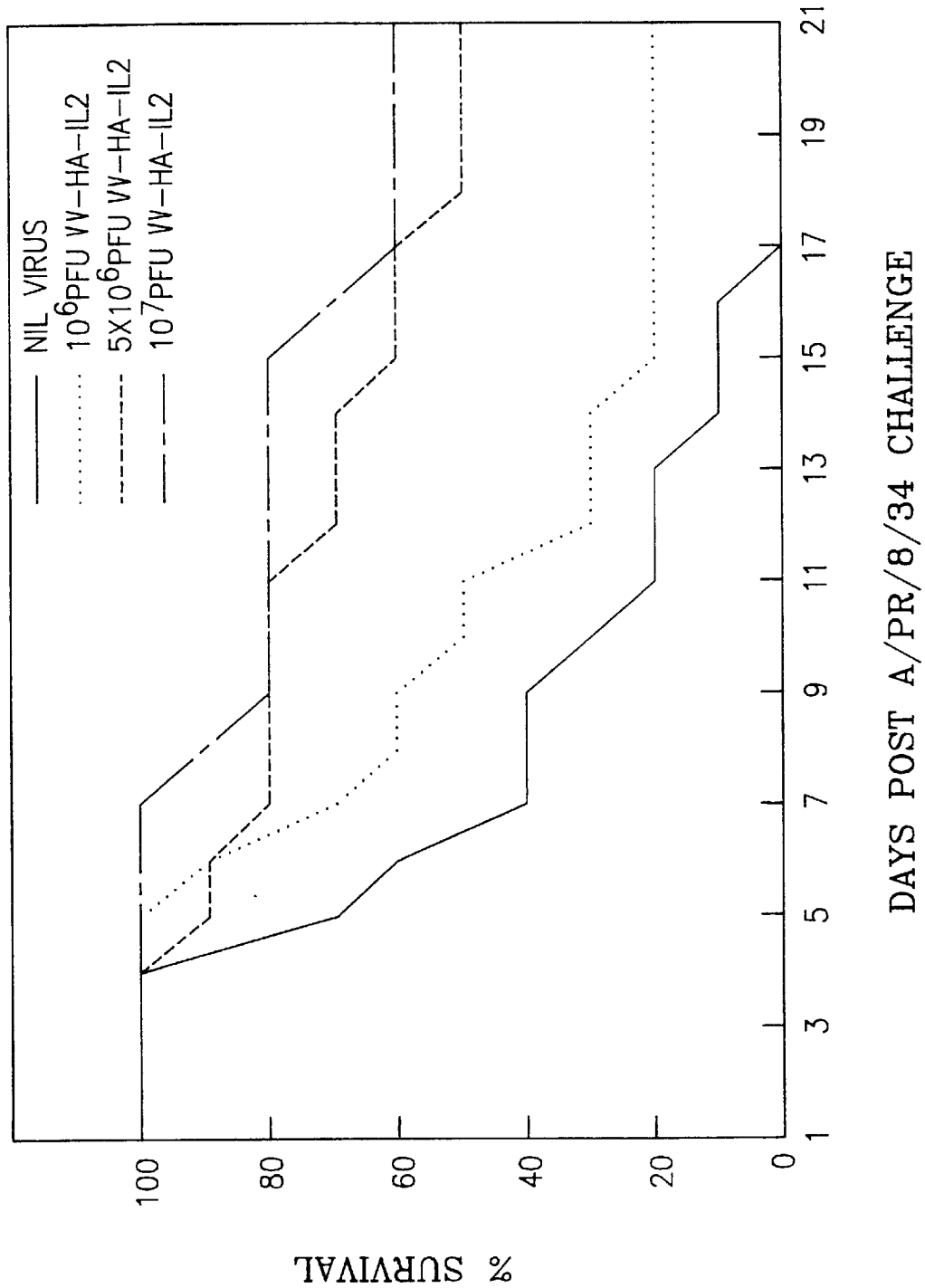
FIG. 9 is a graph which shows the percent survival over a period of time for groups of Swiss outbred nude mice which were inoculated with VV-HA-IL2 at various doses and which were challenged after 30 days with 10 $LD_{50}$ of A/PR/8/34; and a control group which was not given any virus.
Figure 10:
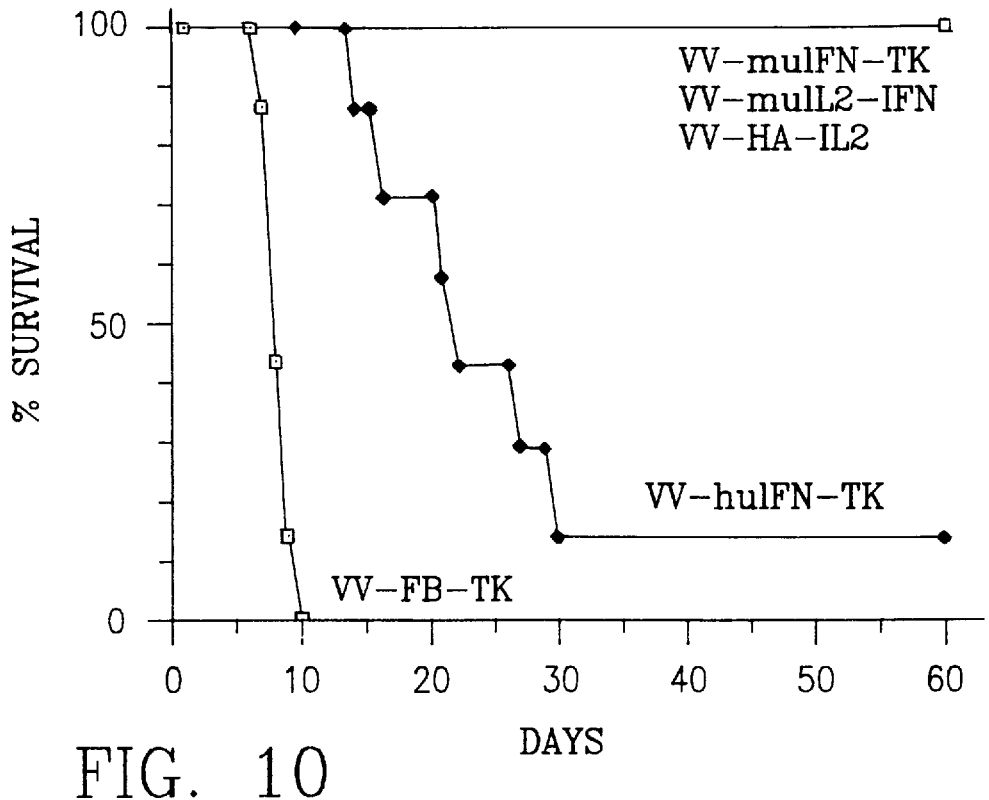
FIG. 10 is a graph which shows the survival over a period of time of athymic Swiss outbred nude mice infected with VV recombinants.
Figure 11:
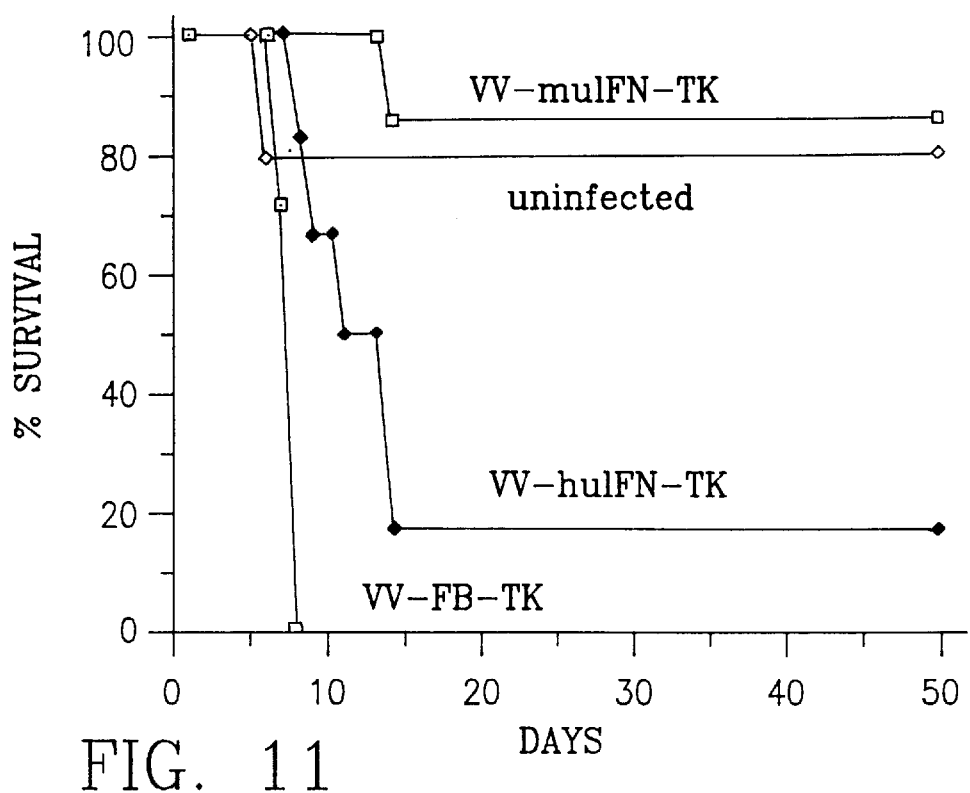
FIG. 11 is a graph which shows the percent survival over a period of time of sublethally irradiated CBA/HI euthymic mice infected with VV recombinants.

Groups of 10 Swiss outbred nude mice were inoculated intravenously with VV-HA-IL2 (see Example 2) at various doses and a control group was not given any virus. After 30 days, all mice were challenged with $10LD_{50}$ of A/PR/8/34 intranasally and mortality recorded. The results are shown in FIG. 9, and show that nude mice that are immunised with VV-HA-IL2 survive the vaccination and develop an immune response that confers some protection against a challenge with influenza virus.

(b) The following Table sets out results demonstrating that VV-HA-IL2 also offers better survival from immunisation with a recombinant vaccinia virus, as compared to VV-HA-TK which does not express IL2, in another model of immunodeficiency, sublethally irradiated (700 R) mice:

Mortality and mean time to death in sublethally irradiated mice after intranasal inoculation.

| Experiment | % Survival[a] | | MTD[b] | |
|---|---|---|---|---|
| | VV-HA-TK | VV-HA-IL2 | VV-HA-TK | VV-HA-IL2 |
| 1 | 0 | 88 | 11.0 | 13.0 |
| 2 | 0 | 100 | 11.4 | — |
| 3 | 0 | 43 | 10.0 | 21.5 |
| 4 | 0 | 57 | 11.2 | 14.0 |
| 5 | 0 | 70 | 10.6 | 15.3 |

[a]Mice were inoculated with $10^7$ pfu virus within 1 hour of irradiation and were monitored for 21 days or until all animals were dead or had recovered.
[b]Mean time to death.
[c]BALB/c mice; CBA/H mice were used in the other experiments.

(c) The following Table sets out results showing that in sublethally irradiated CBA/H mice, immunisation with VV-HA-IL2 confers some protection against a subsequent challenge with A/PR/8/34 influenza virus (see Experiment 1). When the dose of vaccinia virus used for immunisation was lowered to allow mice to survive immunisation with viruses that did not express IL2, it can be seen that VV-HA-IL2 does not confer better protection against influenza virus than VV-HA-TK (see Experiment 2) indicating that IL2 is not increasing the protective immunity, but is allowing the immunodeficient mice to survive a full dose of the vaccine and the surviving mice do have protective immunity. Experiment 3, again with a lower dose of virus, demonstrates that the recombinant viruses do provide protective immunity against subsequent challenge with vaccinia virus.

Protective immunity in VV-HA-IL2-recovered, sublethally irradiated mice.

| Immunizing Virus[a] | Challenge Virus[b] | % Survival | MTD[c] | Morbidity |
|---|---|---|---|---|
| Experiment 1 | | | | |
| $10^7$ pfu VV-HA-IL2 | 100 $LD_{30}$ A/PR/8/34 | 71 | 11.5 | + |
| NIL | 100 $LD_{30}$ A/PR/8/34 | 0 | 6.6 | ++ |
| $10^7$ pfu VV-HA-IL2 | 10 $LD_{30}$ A/PR/8/34 | 86 | 9.0 | + |
| NIL | 10 $LD_{30}$ A/PR/8/34 | 0 | 8.7 | ++ |
| Experiment 2 | | | | |
| $10^5$ pfu VV-HA-IL2 | 10 $LD_{30}$ A/PR/8/34 | 80 | 9.0 | + |
| $10^5$ pfu VV-HA-TK | 10 $LD_{30}$ A/PR/8/34 | 80 | 9.5 | + |
| $10^5$ pfu VV-KD-B2M | 10 $LD_{30}$ A/PR/8/34 | 22 | 9.0 | ++ |
| Experiment 3 | | | | |
| $10^5$ pfu VV-HA-IL2 | $10^5$ pfu VV-WR | 100 | — | +/− |
| $10^5$ pfu VV-HA-TK | $10^5$ pfu VV-WR | 100 | — | +/− |
| NIL | $10^5$ pfu VV-WR | 10 | 8.7 | ++ |

[a]Groups of 7–10 sublethally irradiated mice were immunized in. with the indicated virus.
[b]Mice were challinged with A/PR/8/34 (in.) or VV-WR (iv.) 3 weeks after immunization.
[c]Mean time to death.

EXAMPLE 7

This example demonstrates that IL2 expressed from a separate virus that infects the same site, but not necessarily the same cell, does not clear virus as efficiently as when all virus expresses IL2. That is, it is important that the IL2 is co-expressed by the virus so that it can be most efficiently delivered.

CBA/H mice were inoculated into a hind footpad with $10^7$ pfu VV-HA-IL2 or $10^6$ pfu VV-HA-TK or a mixture of the two viruses. Feet were removed 15 days later and assayed for virus. The results are shown in the following Table:

| VIRUS | CLEARED TOTAL/(%) |
|---|---|
| VV-HA-IL2 + VV-HA-TK | 2/13 (15.4) |
| VV-HA-IL2 | 10/18 (55.6) |
| VV-HA-TK | 1/14 (7.1) |

EXAMPLE 8

This example demonstrates the augmentation of vaccinia virus-specific IgA by IL5, and shows that IL5 increases the secondary IgA levels of antibody that are specific for vaccinia virus. The increase in total antibody probably reflects the increase in IgA and other data indicate that other classes of antibody are not increased by IL5.

Antibody was assayed by ELISA, using whole vaccinia virus as the antigen. A serum containing vaccinia-specific antibody was used to construct a standard curve with the vaccinia-specific antibody titre expressed as arbitrary units.

CBA/H mice were inoculated intravenously with $10^7$ pfu vaccinia virus and bled 14 days later for primary antibody. On day 28 after primary inoculation, the mice. were re-inoculated with the same dose of virus and were bled 7 days later for assay of secondary antibody. In the following table, mean titres of groups of 5 mice are shown with the range of values in brackets.

| VIRUS | IpA | TOTAL ANTIBODY |
|---|---|---|
| Primary | | |
| VV-IL5 | 444 | 1255 |
| | (<125–1447) | (733–1846) |
| VV-HA | 309 | 522 |
| | (<125–1200) | (469–856) |

-continued

| VIRUS | IpA | TOTAL ANTIBODY |
|---|---|---|
| Secondary | | |
| VV-1L5 | 31,550 | 56,436 |
| | (6,500–100,000) | (18,350–95,238) |
| VV-HA | 5,155 | 40,254 |
| | (800–11,400) | (10,825–98,039) |

VV-HA has been described previously (26). VV-IL5 was constructed from plasmid pEDFM-5 (obtained from Dr. I. Young, John Curtin School of Medical Research, Australian National University) containing the murine IL-5 sequence (45). The plasmid was cut with HinPI at sites 24 and 650 of the gene and cloned into the Acc I site of pBCB07 (25,38). The EcoR1 fragment with the p7.5 promoter was then cloned into the EcoR1 site of pFBX. pFBX-IL-5 was then marker rescued into VV-PR8-HA6 to make VV-IL5.

EXAMPLE 9

This example demonstrates that by inclusion of the gene for murine IFN-γ in a recombinant vaccinia virus (VV), marked attenuation and reduction in pathogenicity can be achieved. VV infection is usually lethal in immunodeficient animals, however it has been found that both athymic nude mice and sublethally irradiated euthymic mice could resolve an infection with VV expressing IFN-γ.

FIG. 10 shows the survival of athymic Swiss outbred nude mice infected with VV recombinants (7 mice per group).

FIG. 11 shows the survival of sublethally irradiated CBA/H euthymic mice infected with VV recombinants (VV-FB-TK, VV-muIFN-γ-TK: 7 mice per group; VV-huIFN-γTK: 6 mice per group; uninfected: 5 mice per group).

MATERIALS AND METHODS a. Construction of VV-μIFN-γ-TK and VV-μIL2-IFN-γ.

The murine IFN-γ (μIFN-γ) cDNA clone (36), in the pcD expression vector, was kindly provided by DNAX Research Institute, Palo Alto, Calif., USA. The whole coding sequence between nucleotide positions 1 and 870 was cut out using Sau 3A and Rsa I and ligated into the Bam HI and Hinc II sites of the pBCB07 vaccinia expression vector (25,38). This plasmid was further digested with Eco RI and the fragment containing the P7.5 vaccinia promoter and the μIFN-γ cDNA coding sequence between positions 1 and 706 was then ligated into the Eco RI site of pFB-TK (27). The recombinant plasmid could then be used in a marker rescue with a VV-WR-TK$^-$ mutant (originated from Dr. B. Moss, NIH, Bethesda, Md., USA) and with VV-IL2, a thymidine kinase (TK) negative recombinant (39), which contains the IL2-expressing gene in the J region of the vaccinia strain VV-WR, interrupting the VV-TK gene. Subsequent plaque purification under methotrexate selection (27) produced two recombinant viruses, VV-μIFN-γ-TK and VV-μIL2-IFN-γ, both of which contained the μIFN-γ gene and the herpes simplex virus (TK) gene in the F region of vaccinia. In subsequent immunological assays the recombinant virus VV-FB-TK (27), was used as a control together with VV-HA-IL2 (see Example 2). In some assays another control virus, VV-huIFN-γ-TK, containing the human IFN-γ gene, was included. The cloning of this cDNA into the pBCB07 vector was carried out as previously described (40) and the virus was constructed through pFB-TK cloning in the same way as VV-μIFN-γ-TK.

b. Bioassay for murine IFN-γ and flow cytometry.

Tissue culture supernatants (2.5 ml) of VV-infected human 143B cells (2×10$^6$ were treated as previously described (40). Induction of MHC antigens was tested on BALB/c mouse embryo fibroblasts (MEF) (41) and a murine myeloid tumour cell line WEHI-3B (42) using flow cytometry (FACS IV; Becton Dickinson). For MEF, 1 ml of each supernatant was added into 1×10$^6$ cells/3 ml medium, and for WEHI-3B, 2 ml of supernatant was added into 0.5×10$^6$ cells/2 ml medium (both subconfluent on 5 cm petridishes). Recombinant murine IFN-γ (rIFN-γ), provided by Boehringer Ingelheim (Vienna, Austria), was used as a positive control. The cells were labelled as previously described (41,40). Monoclonal antibodies against $K^d/D^d$ (HB-79) and $Ia^d$ (HB-3) were obtained from American Type Culture Collection.

c. Mice.

CBA/H (H-2$^k$), BALB/c (H-2$^d$) and athymic Swiss outbred nude mice were bred at the John Curtin School of Medical Research, Australian National University, under specific pathogen-free conditions.

RESULTS a. Bioassay of VV-expressed murine IFN.

Tissue culture supernatants, harvested 12–14 h after infection of human 143B cells with VV (5 pfu/cell), were tested for their ability to induce MHC class I and class II antigens on MEF and WEHI-3B cells, respectively. After 48 h of incubation, VV-μIFN-γ-TK supernatant caused a clear increase in MHC expression on MEF, whereas VV-FB-TK and VV-huIFN-γ-TK supernatant treated cells expressed the same levels of MHC as those without any treatment. For WEHI-3B, untreated control cells showed two peaks, one of which disappeared with rIFN-γ, VV-μIFN-γ-TK and VV-μIL2-IFN-γ supernatant treatments, indicating induction of MHC class II antigens. Again, VV-FB-TK and VV-huIFN-γ-TK supernatant treated cells were identical with the control treated cell population. Thus, the IFN-γ secreted by VV-μIFN-γ-TK and μIL2-IFN-γ infected cells was biologically active on murine but not on human 143B cells, where class I expression could be induced with human rIFN-γ or VV-huIFN-γ-TK supernatant (data not shown).

b. Infection of immunodeficient athymic nude mice and sublethally irradiated euthymic mice with recombinant vaccinia viruses.

9-week old athymic nude mice were injected i.v. with 5×10$^6$ pfu of VV recombinants and their survival monitored daily (FIG. 10). The mean survival of mice injected with control virus (VV-FB-TK) was 8.4 days, whereas all VV-μIFN-γ-TK, VV-μIL2-IFN-γ and VV-HA-IL2 infected mice survived infection and lived for several months. For VV-huIFN-γ-TK, one mouse recovered from infection and the mean survival for the rest was 21.7 days.

9-week old CBA/H euthymic mice were given a sublethal dose (650R) of gamma irradiation and then injected i.v. with each of the recombinant VV (10$^7$ pfu). Again, all VV-FB-TK and all except one VV-huIFN-γTK infected mice died early after infection (mean survival 7.7 days and 11.2 days respectively). Only one VV-μIFN-γ-TK infected and one uninfected control mouse died, but the rest survived for the several weeks of the experiment (FIG. 11).

c. Recombinant virus growth in mouse organs.

7-week old female CBA/H mice were injected i.v. with 10$^7$ pfu of VV recombinants. Groups of four mice were killed daily and their ovaries collected for virus titration. Ovaries were chosen for analysis because it has previously been shown that they are a very sensitive indication of attenuated virus growth. VV-FB-TK grew to very high titres in the ovaries reaching titres of 10$^{8.2}$ by day 3; however, by day 10 almost all the virus was cleared. VV-huIFN-γ also grew to high titres but was cleared slightly faster than VV-FB-TK. In contrast, the peak virus titre reached with VV-μIFN-γ-TK and VV-μIL2-IFN-γ was $10^{4.8}$ and $10^{2.8}$, respectively, on day 2, and by day 4 the mice had completely resolved the infection.

EXAMPLE 10

This example demonstrates the construction of a recombinant vaccinia virus which encodes the gene for murine tumour necrosis factor (TNF)-α, and shows that the localised production of TNF-α during a viral infection leads to the rapid and efficient clearance of the recombinant virus in normal mice and attenuates the otherwise lethal pathogenicity of the virus in immunodeficient animals.

Figure 12A:
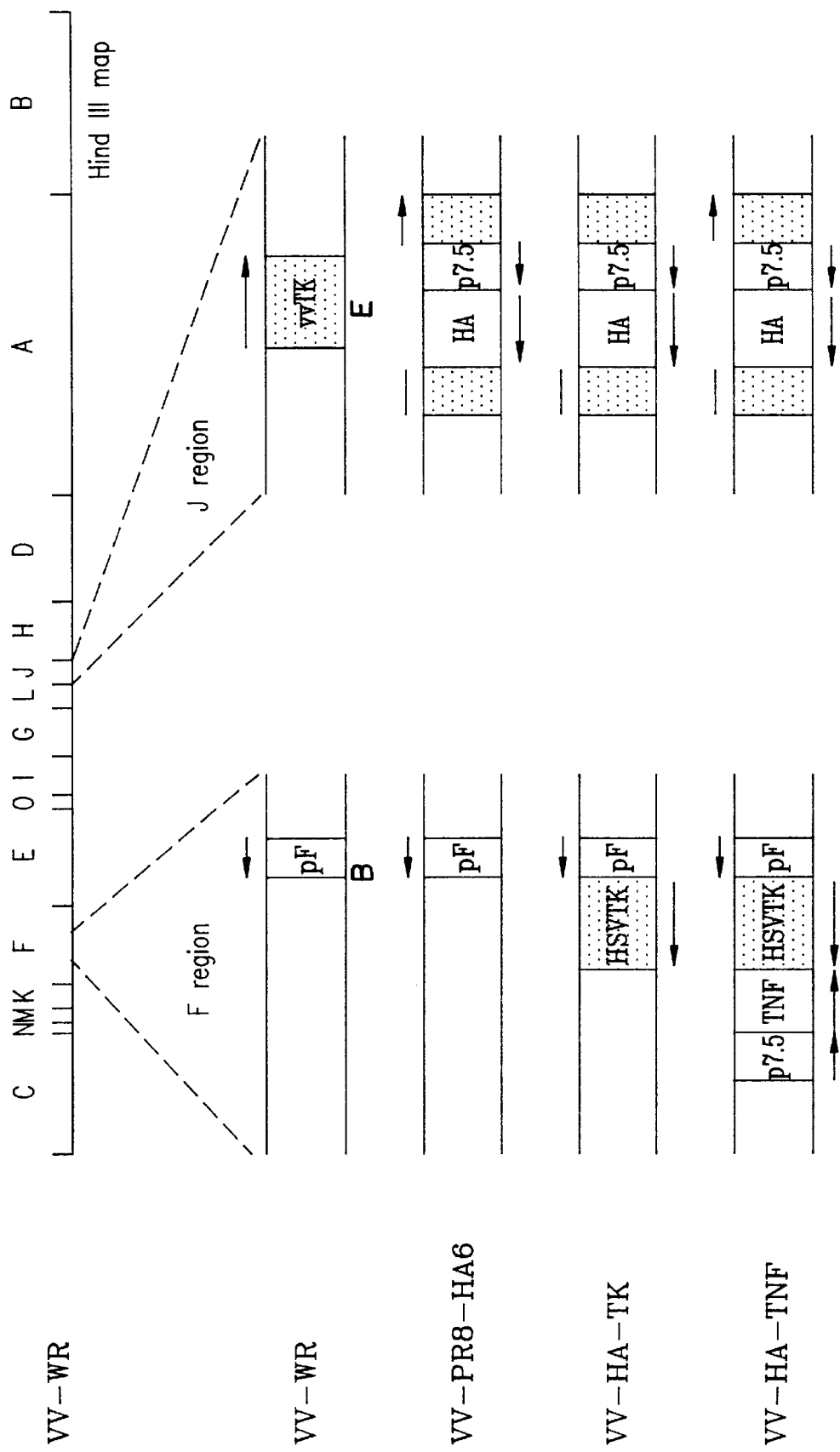
FIG. 12a shows the genomic configuration of VV recombinants.
Figure 12B:
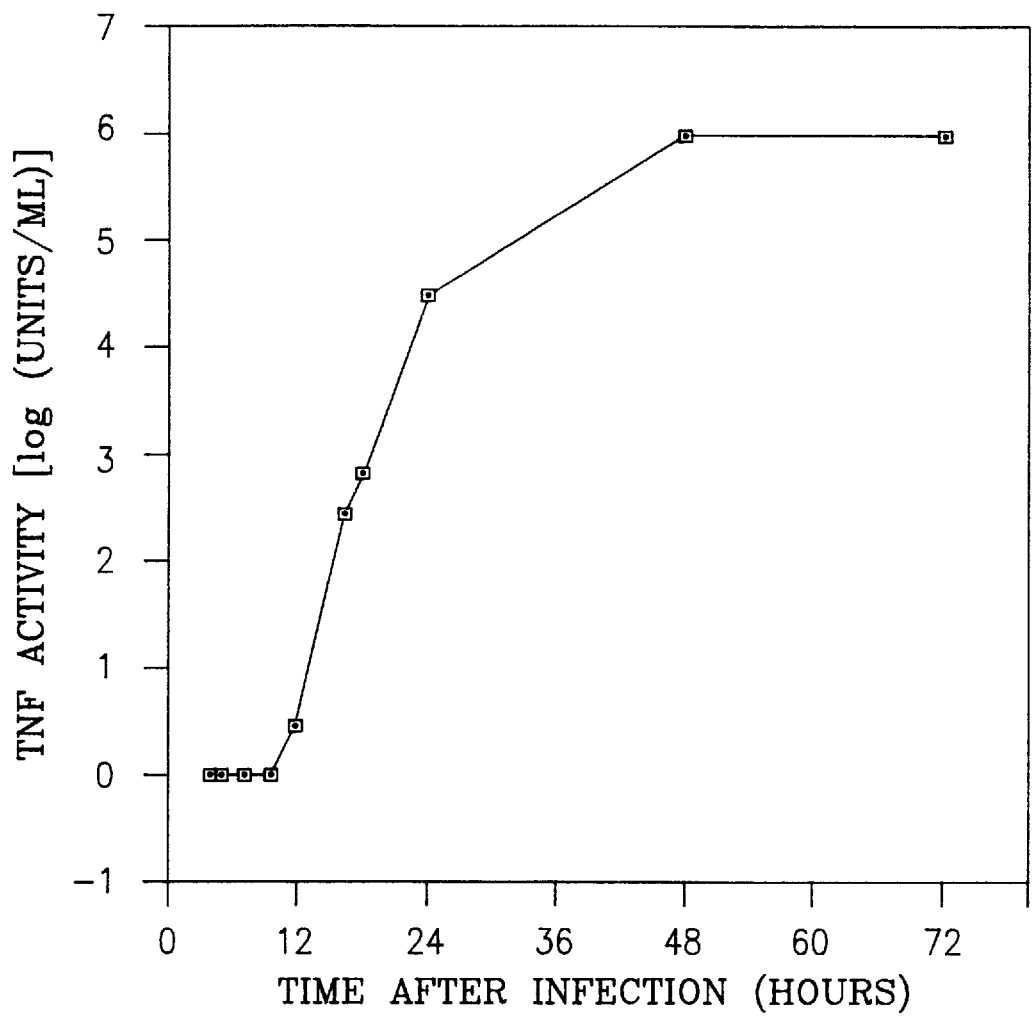
FIG. 12b is a graph which shows the expression of biologically active TNF over a period of time by VV-HA-TNF-infected cells.

FIGS. 12A and 12B show:

(a) Genomic configuration of VV recombinants.

A HindIII map of VV strain WR (VV-WR) is shown with insertion points at the BamHI (B) and EcoRI (E) sites in the F and J regions respectively. Arrows indicate orientations of VV thymidine kinase gene (vvTK), VV promoters (p7.5 and PF) and inserted genes. VV-PR8-HA6 (described previously as VV-HA), a L929 cell line adapted strain of VV-WR containing the haemagglutinin gene of influenza virus, A/PR/8/34 in the J region, was used to construct the recombinant viruses used in this study. The recombinant virus VV-HA-TNF contains within the F region the whole cDNA coding sequence including signal peptide for murine TNF-α (cDNA supplied by Prof. W. Fiers, State University of Ghent, Belgium) under the control of the VV 7.5 kDa promoter, p7.5 (provided by Dr. B. Moss, NIH), along with the thymidine kinase gene of herpes simplex (HSV-TK) which was used as a selectable marker. The control virus, VV-HA-TK (described previously), similarly contains the HSV-TK gene but not TNF-α cDNA in the F region.

(b) Assay for expression of biologically active TNF by VV-HA-TNF-infected cells. Confluent monolayers of the human osteosarcoma cell line, 143B were infected with the VV recombinants at 5 pfu/cell in 6 well multidishes. At the indicated time points, the supernatants from duplicate wells; were harvested, filtered through 0.2 μm filters twice and frozen. Samples were assayed using the TNF-sensitive fibrosarcoma cell line WEHI164 treated with 2 μg/ml of Actinomycin D, and a colorimetric method to quantify cell death using the tetrazolium salt, MTT. TNF units were calculated from a standard curve generated with serially diluted recombinant human TNF-α (Chiron, USA, specific activity= $5 \times 10^7$ Units/mg).

Figure 13A:
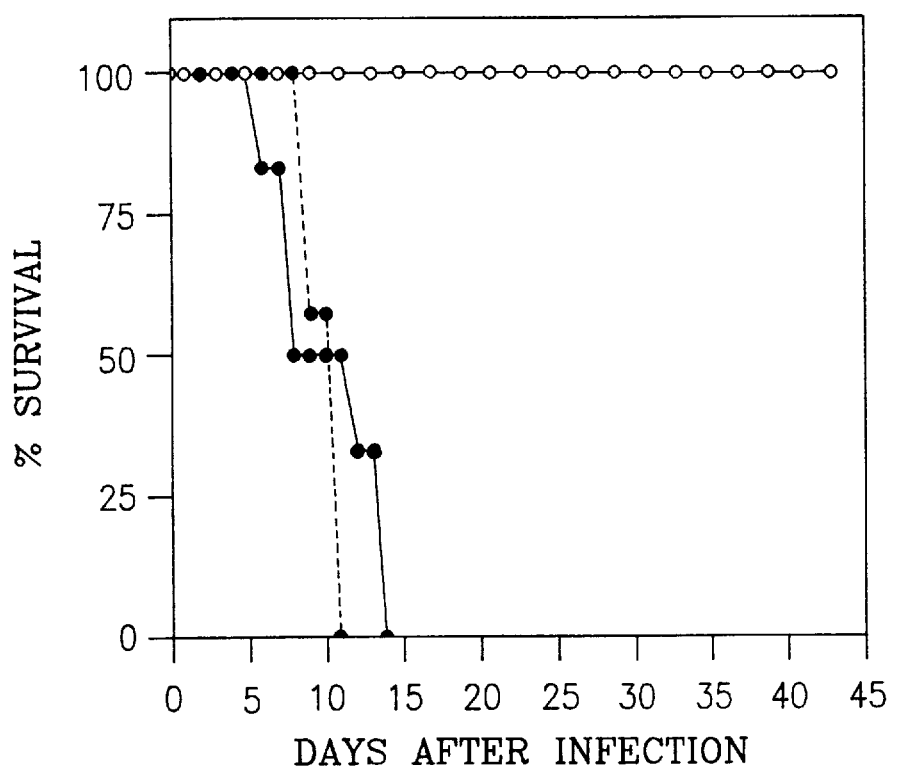
FIG. 13a is a graph which shows the percent survival over a period of time with respect to immunodeficient mice which have been inoculated with VV-recombinants.
Figure 14:
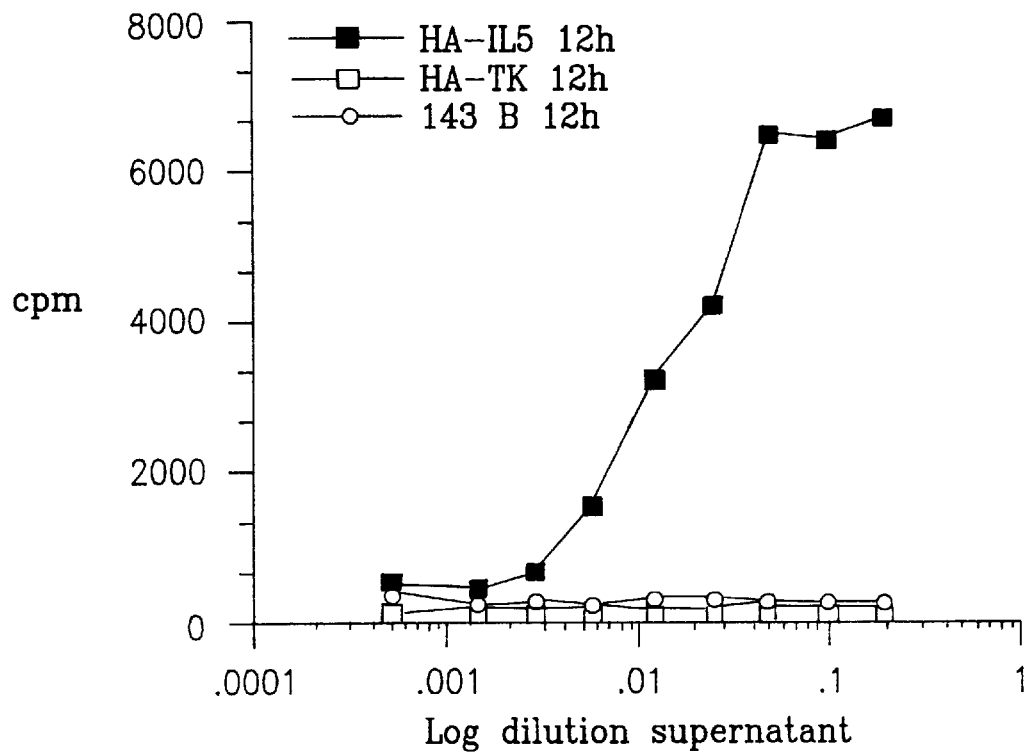
FIG. 14 is a graph which shows that 12 hour supernatants from VV-HA-IL5-infected 143B cells stimulated $BCL_1$, to proliferate in a dose-dependent manner.
Figure 15:
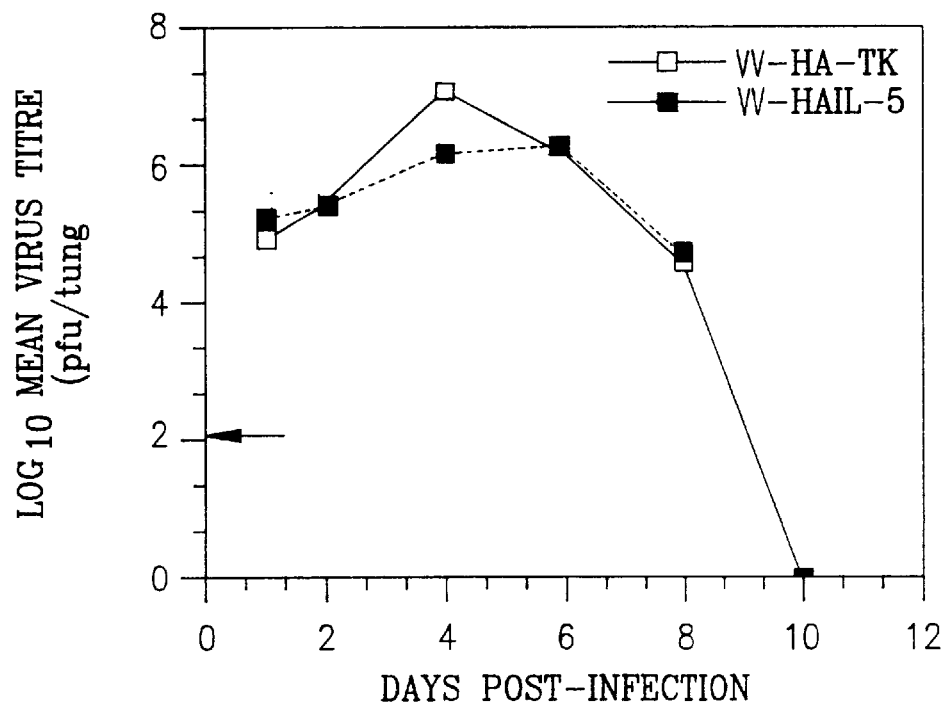
FIG. 15 is a graph which shows the mean virus titre over a period of time after infection with VV-HA-IL5 and VV-HA-TK.
Figure 16:
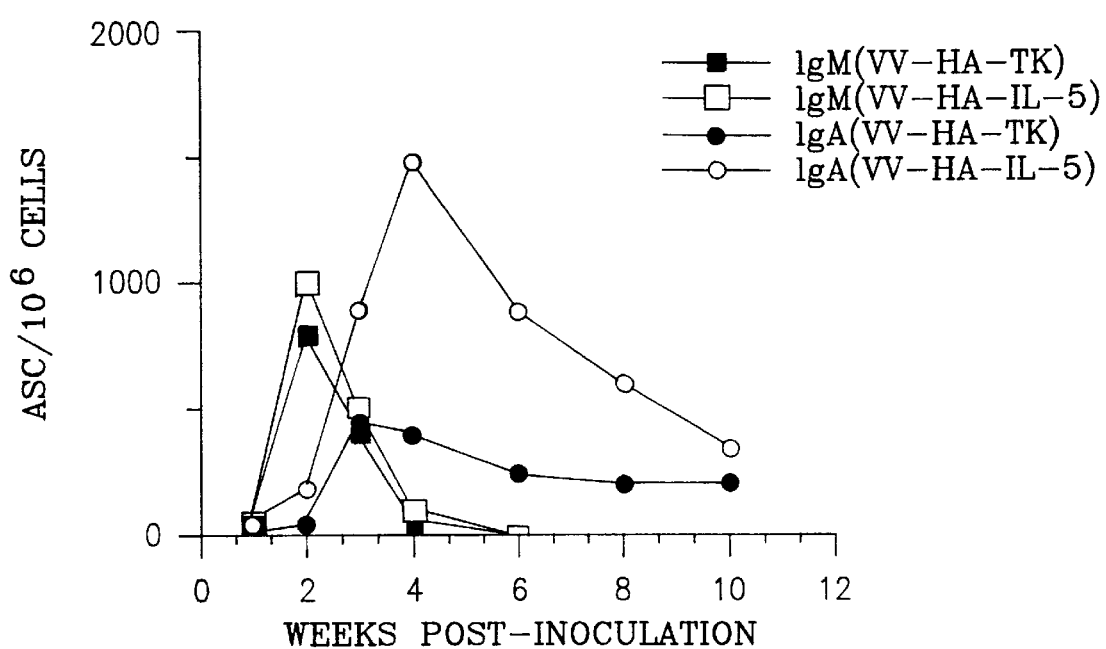
FIG. 16 is a graph which shows the number of specific antibody-secreting cells (ASC) as a function of time after intranasal inoculation with $10^7$ plaque-forming units of virus at day 0.

FIGS. 13A and 13B show the attenuation of the VV-HA-TNF in vivo:

(a) Survival study of immunodeficient mice inoculated with VV-recombinants. Groups of 9 week old Swiss outbred nude and 8 week old sublethally (S/L) irradiated mice were inoculated intravenously (i.v.) with the recombinant viruses at a dose of $5 \times 10^6$ pfu and $1 \times 10^7$ pfu respectively. Mortality of VV-HA-TK infected nude (-●-) and S/L irradiated (--●--) mice and the survival of VV-HA-TNF infected nude, VV-HA-TNF infected S/L irradiated and uninfected control mice (-○-) are shown.

(b) Growth kinetics of the VV recombinants in normal mice. Groups of 9-week old female CBA/H mice were injected i.v. with a non-lethal dose, $10^7$ pfu, of either VV-HA-TNF or VV-HA-TK. On the indicated days, selected organs were collected for titration of virus on 143B cell monolayers. Error bars indicate standard errors of the mean titre for groups of 4 mice.

The recombinant viruses (VV-HA-TNF and VV-Ha-TK used in this study were constructed using VV vectors and homologous recombination and selection methods as described previously (43) (FIG. 12a). High levels of TNF were detected in vitro following infection of 143B cell monolayers with the VV-HA-TNF virus (FIG. 12b), indicating effective vector-directed expression and secretion of biologically active TNF as measured by a cytotoxicity assay (44).

In order to compare the in vitro replicative efficacy of VV-HA-TNF to that of the control virus, VV-HA-TK, a single-step growth experiment (multiplicity of infection (MOI)=5 pfu/cell) was performed. Under these conditions, growth profiles for both recombinant viruses were similar in either CV-1 (simian) or L929 (murine) cell lines (data not shown). This indicates that the ability of VV-HA-TNF to replicate in vitro at high MOI, is not altered by insertion of the TNF gene or by the expression of TNF. To test the sensitivity of VV to the antiviral effects of TNF, the cell lines, L929, 143B, 293, HeLa and primary rat embryo fibroblasts were pretreated with 0.1–400 ng/ml recombinant murine TNF-α (Genentech, specific activity=$1.2 \times 10^7$ Units/mg, supplied by Boehringer Ingelheim) or human TNF-α (Asahi, specific activity=$2.2 \times 10^6$ Units/mg) for 24 h and then infected with VV-WR (wild type). When the virus yield was measured 24 h later, only L929 cells showed reduced virus growth (up to 1.5 log) in the presence of TNF. Some toxicity towards the L929 cells was noted, however, at the concentration of TNF required to inhibit virus replication.

In contrast to these In vitro results, which suggest that VV is not highly susceptible to the antiviral effects of TNF, expression of TNF markedly attenuated the growth of VV-HA-TNF in vivo (FIG. 13). Two models of immunodeficiency were used: athymic Swiss outbred nude mice and euthymic CBA/H mice rendered immunodeficient by a sublethal dose of γ-irradiation (650 R) administered 24 h prior to infection. Both the nude and irradiated mice infected with the control virus, VV-HA-TK, died from a disseminated vaccinial disease, with a mean survival time of approximately 10 days (FIG. 13a). In contrast, when infected with VV-HA-TNF, both groups of mice survived and remained as healthy as the uninfected controls, indicating that TNF expression had reduced the pathogenicity of VV in these mice (FIG. 13a).

The attenuating effect of TNF expression on virus growth was also seen in normal mice (FIGS. 13b–13e). Neither VV-HA-TNF, nor its control, VV-HA-TK, produced morbidity or mortality at the doses used. However, VV-HA-TNF was recovered from various organs at significantly reduced titres and the virus cleared more rapidly as compared to VV-HA-TK (FIGS. 13b–13e). The difference in growth between the two viruses was evident by 24 h post-infection (p.i.) (FIGS. 13b–13e) and even earlier in some cases (data not shown). Growth in the ovaries provided one of the most prominent indicators of virus attenuation. VV-HA-TK grew to very high titres, reaching $10^{8.1}$ pfu per pair of ovaries by day 3, and was cleared only by day 10, whereas VV-HA-TNF reached a mean peak titre of $10^{3.5}$ pfu per pair of ovaries and was cleared 3–5 days p.i.. Histological examination of the ovaries from mice infected with W-HA-TK revealed extensive damage to the stromal tissue and follicles, whereas those from VV-HA-TNF infected mice appeared normal (data not shown).

EXAMPLE 11

This example compares the effect of administration of exogenous recombinant IL-2 or recombinant IFN-γ on the growth of vaccinia virus with the effects of co-expressed IL-2 (VV-HA-IL2).

Groups of 3 to 5 outbred nude mice infected i.v. with $10^7$ pfu VV-HA-TK were given 600 U of rIL-2 or rIFN-γ i.p. every 8 h for a period of 5 days. Morbidity and mortality in these groups and others given virus alone or the recombinant cytokines alone was assessed. No morbidity or mortality was recorded in groups of mice given only rIL-2 or rIFN-γ. All mice given VV-HA-IL2 alone survived with no overt disease. Nude mice infected with VV-HA-TK alone showed signs of disease by 6 days p.i. and all mice died with a MTD of 12.2 days. Treatment with exogenous rIL-2 or rIFN-γ delayed the onset of disease signs which appeared between 11–16 days p.i., and significantly ($p < 0.001$) prolonged survival of nude mice. Nevertheless, all mice that had been infected with VV-HA-TK and treated with either rIL-2 or rIFN-γ succumbed to disseminated disease and died with MTD of 23.4 and 25.8 days, respectively.

The survival rates are summarised in the following Table:

| TREATMENT | VV-HA-IL2 | VV-HA-TK (Control) |
|---|---|---|
| nil | 5/5 survivors | 0/5 survivors |
| rIL-2 600 U every 8 hrs for 5 days | ND | 0/5 survivors |
| rIFN-γ 600 U every 8 hrs for 5 days | ND | 0/5 survivors |

EXAMPLE 12

In this example, a recombinant vaccinia virus (VV-HA-IL5) expressing IL-5 in combination with the haemagglutinin of influenza virus PR8 (HA) is constructed using the methods described in Example 1. Thus, the HA gene was inserted in the J region of vaccinia virus strain WR (see FIG. 2), and the genes for murine IL-5 (45) and thymidine kinase of HSV in the F region.

The leukaemic B cell line $BCL_1$, which responds to IL-5 by proliferating, was used to test for expression of IL-5 by the construct. FIG. 14 shows that 12 hour supernatants from VV-HA-IL5-infected 143B cells stimulated $BCL_1$ to proliferate in a dose-dependent manner, unlike those from uninfected 143 B cells or from cells infected with the control virus, VV-HA-TK, which encodes HA but not IL-5.

In time-course experiments to assess virus growth in vivo, it was found that both VV-HA-IL5 and VV-HA-TK exhibit similar growth kinetics in murine lung when administered intranasally (FIG. 15).

IL-5 activity in vivo was assessed by examining the influence of VV-encoded IL-5 on the immune response to co-expressed HA in vivo, in terms of numbers of HA-specific antibody-secreting cells (ASC). This parameter was chosen as most likely to reflect IL-5 activity, given existing evidence from in vitro studies that this factor appears to act in promoting terminal differentiation of B cells. The ELISPOT assay was used to enumerate HA-specific antibody-secreting cells. This assay detects specific antibody secreted by each cell as an insoluble spot on nitrocellulose membrane.

No elevation in numbers of anti-HA ASC of IgM, G or A isotypes were detected in either lungs or spleen of mice given VV-HA-IL5 intravenously compared with those given control virus (data not shown). Similarly, IgM or IgG ASC levels in the lung were unaffected following intranasal inoculation. However, following intranasal inoculation, numbers of anti-HA IgA ASC in lungs were up to 4-fold higher in mice given VV-HA-IL5 (FIG. 16—mice given intranasally $10^7$ plaque-forming units of virus at day 0). These differences became apparent by day 16 after infection and persisted for over 3 weeks.

In vitro evidence supporting the concept that IL-5 is acting to increase ASC numbers by increasing differentiation of committed membrane IgA-positive cells to plasma cells is shown in the following table. Mice were primed with influenza virus PR8 and lung cells were isolated 14 days later, T-depleted, fractionated by panning and cultured for 4 days. Both unfractionated B cells and $mIgA^+$ cells cultured with recombinant IL-5 displayed increased ASC numbers, unlike the mIgA $^{31}$ fraction.

TABLE

Effect of rIL5 on IgA ASC numbers in immunised lung.

| inoc. | restim | Total IgA ASC/$10^6$ cells cultured | | |
|---|---|---|---|---|
| in vivo | in vitro | B cells | mIgA+ | $mIgA^-$ |
| PR8 | none | 200 ± 60 | 1220 ± 220 | 20 ± 10 |
| PR8 | rIL-5 (5 u/ml | 520 ± 125 | 3750 ± 435 | 30 ± 12 |
| none | rIL-5 | 220 ± 80 | 1590 ± 450 | 35 ± 20 |

The above data provides evidence for the ability of IL-5 co-expressed with HA in recombinant VV to augment IgA responses to HA in vivo. As IgA functions in virus neutralisation at the most common point of infection, i.e. the mucosae, such responses may afford increased protection.

REFERENCES

1. Howard, M. et al. J. Exp. Med. 157, 1529–1534 (1983).
2. Baracos, V. et al. New Eng. J. Med. 308, 553–558 (1983).
3. Schmidt, J. A. et al. J. Immun. 128, 2177–2182 (1982).
4. Mizel, S. B. in Biological Response in Cancer (ed. Mihich E.) 89–119 (Plenum, N.Y. 1982).
5. Lomedico, P. T. et al. Nature 312, 458–461 (1984).
6. Auron, P. E. et al. Proc. Natl. Acad. Sci. US 81, 7907–7911 (1984).
7. Smith, K. A. Ann. Rev. Immunol. 2, 319–333 (1984).
8. Minato, N. et al. J. Exp. Med. 154, 750 (1983).
9. Tsudo, M. et al. J. Exp. Med. 160, 612–616 (1984).
10. Merluzzi, V. J. et al. Cancer Res. 41, 850–853 (1981).
11. Wagner, H. et al. Nature 284, 278–80 (1982).
12. Vose, B. M. et al. Cancer Immuno. 13, 105–111 (1984).
13. Rosenberg, S. A. et al. Science 233, 1318–1321 (1986).
14. Yokota, T. et al. Proc. Natl. Acad. Sci. USA 82, 68–72 (1985).
15. Taniguchi, T. et al. Nature, 302, 305–307 (1983).
16. Schroder, T. W. et al. in Contemporary Topics in Molecular Immunology: The interleukins, eds Gillis, S. and Inman, F. P. (Plenum, N.Y.) Vol. 10, pp. 121–146 (1985).
17. Yokota, T. et al. Proc. Natl. Acad. Sci. USA 81, 1070–1074 (1984).
18. Sevenusar, E. Eur. J. Immunol. 17, 67–72 (1987).
19. Lee, F. et al. Proc. Natl. Acad. Sci. USA 83, 2061–2065 (1986).
20. Yokota, T. et al. Proc. Natl. Acad. Sci. USA 83, 5894–5898 (1986).
21. Gray, P. W. et al. Nature 295, 503–508 (1982).
22. Smith, G. L. et al. Nature 302, 490–495 (1983).
23. Hu, S. L. et al. Nature 320, 537–540 (1986).
24. Boyle, D. B. and Coupar, B. E. H. J. Gen. Virol. 67. 1591–1600 (1986).

25. Boyle, D. B. et al. Gene 35, 169–177 (1985).
26. Andrew, M. E. et al. Microbial Pathogenesis 1, 443–452 (1986).
27. Coupar, B. E. H. et al. J. Gen. Virol. 68, 2299 (1987).
28. Coupar, B. E. H. et al. Gene 68, 1–10 (1988).
29. Gillis S. et al. J. Immunol 120, 2027–2032 (1978).
30. Mosmann, J., J. Immunol. Meth. 65, 55–63 (1983).
31. Cutt, J. R. et al. J. Virol. 61, 543 (1987).
32. Wright, D. C. et al, New Eng. J. Med. 316, 673–675 (1987).
33. Kierny, M. P. et al. Biotechnology 4, 790–795 (1986).
34. Andrew, M. E. et al. Scand. J. Immunol. 25, 21–28.
35. Smith, G. L. et al. Proc. Natl. Acad. Sci. 80, 7155–7159.
36. Gray, P. W. et al. Proc. Natl. Acad. Sci. USA, 80, 5852 (1983).
37.
38. Andrew, M. E. et al. J. Virol. 61, 1054, (1987).
39. Mullbacher, A. et al. Scand. J. Immunol., 29, 1, (1989).
40. Kohonen-Corish, et al. J. Immunol., 143, 623, (1989).
41. King, N. J. C. et al. Expl. Clin. Immunogenet., 2, 206, (1985).
42. Wong, G. H. W. et al. J. Immunol., 131, 788, (1983).
43. Ramshaw, I. A. et al. Nature, 329, 545–546 (1987).
44. Espevik, T. et al. J. Immun. Methods, 95, 99–105, (1986).
45. Kinashi, T. et.al.. Nature 324, 70–73 (1986).

What is claimed is:

1. A preparation for stimulating an immune response to an antigenic polypeptide in a human or animal host, comprising a vector for expressing an antigenic polypeptide in said human or animal host, said vector incorporating a first nucleotide sequence which is expressed as said antigenic polypeptide, together with a second nucleotide sequence which is expressed as a polypeptide having lymphokine activity and which is effective in enhancing the immune response in said human or animal host to the antigenic polypeptide when compared to the immune response in said human or animal host administered a vector incorporating only the first nucleotide sequence, wherein said polypeptide having lymphokine activity is co-expressed with said antigenic polypeptide in said human or animal host.

2. A preparation according to claim 1, wherein the antigenic polypeptide is foreign to the vector.

3. A preparation according to claim 1, wherein the polypeptide having lymphokine activity is selected from the group consisting of interleukin-1, interleukin-2, interleukin-3, interleukin-4, interleukin-5, γ-interferon and tumour necrosis factor.

4. A preparation according to claim 1, wherein the first nucleotide sequence is expressed as an antigenic polypeptide of the human immunodeficiency virus.

5. A preparation according to claim 1, wherein the first nucleotide sequence is expressed as an antigenic polypeptide of the influenza virus.

6. A preparation according to claim 1 wherein said vector is a virus.

7. A preparation according to claim 6, wherein the virus is selected from the group consisting of poxvirus, herpes virus and adenovirus.

8. A preparation according to claim 7, wherein said virus is a poxvirus.

9. A preparation according to claim 8, wherein said virus is vaccinia virus.

10. A method of stimulating an immune response to an antigenic polypeptide in a human or animal host, which comprises the step of administering to the human or animal host a preparation according to claim 2.

11. A preparation according to claim 2, wherein the polypeptide having lymphokine activity is selected from the group consisting of interleukin-1, interleukin-2, interleukin-3, interleukin-4, interleukin-5, γ-interferon and tumour necrosis factor.

12. A preparation according to claim 2, wherein the first nucleotide sequence is expressed as an antigenic polypeptide of the human immunodeficiency virus.

13. A preparation according to claim 2, wherein the first nucleotide sequence is expressed as an antigenic polypeptide of the influenza virus.

14. A preparation according to claim 2, wherein said vector is a virus.

15. A preparation according to claim 4, wherein the virus is selected from the group consisting of poxvirus, herpes virus and adenovirus.

16. A method for the production of the preparation according to claim 2, which comprises the step of inserting into said vector a first nucleotide sequence which is expressed as an antigenic polypeptide which is foreign to the vector, together with a second nucleotide sequence which is expressed as a polypeptide having lymphokine activity and which is effective in enhancing the immune response in said human or animal host to the antigenic polypeptide when compared to the immune response in said human or animal host administered a vector incorporating only the first nucleotide sequence wherein said polypeptide having lymphokine activity is co-expressed with said antigenic polypeptide in said human or animal host.

17. A method of stimulating an immune response to an antigenic polypeptide in a human or animal host, which comprises the step of administering to the human or animal host a preparation according to claim 1.

* * * * *